(12) United States Patent
Wilson et al.

(10) Patent No.: US 11,019,327 B2
(45) Date of Patent: *May 25, 2021

(54) ENDOSCOPE EMPLOYING STRUCTURED LIGHT PROVIDING PHYSIOLOGICAL FEATURE SIZE MEASUREMENT

(71) Applicant: CapsoVision, Inc., Saratoga, CA (US)

(72) Inventors: Gordon C. Wilson, San Francisco, CA (US); Kang-Huai Wang, Saratoga, CA (US); Ganyu Lu, Palo Alto, CA (US)

(73) Assignee: CAPSOVISION, INC., Saratoga, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/726,920

(22) Filed: Dec. 25, 2019

(65) Prior Publication Data

US 2020/0137374 A1 Apr. 30, 2020

Related U.S. Application Data

(63) Continuation of application No. 15/927,856, filed on Mar. 21, 2018, now Pat. No. 10,531,074, and a continuation-in-part of application No. 14/884,788, filed on Oct. 16, 2015, now Pat. No. 9,936,151.

(51) Int. Cl.
| | |
|---|---|
| *H04N 7/18* | (2006.01) |
| *H04N 13/254* | (2018.01) |
| *H04N 9/04* | (2006.01) |
| *H04N 5/225* | (2006.01) |
| *H04N 17/00* | (2006.01) |
| *A61B 1/00* | (2006.01) |
| *A61B 1/04* | (2006.01) |

(52) U.S. Cl.
CPC ....... *H04N 13/254* (2018.05); *A61B 1/00096* (2013.01); *A61B 1/041* (2013.01); *H04N 5/2254* (2013.01); *H04N 5/2259* (2013.01); *H04N 9/045* (2013.01); *H04N 9/04557* (2018.08); *H04N 17/002* (2013.01); *H04N 2005/2255* (2013.01)

(58) Field of Classification Search
CPC .. H04N 13/254; H04N 5/2254; H04N 17/002; H04N 5/2259; H04N 9/045; H04N 2005/2255; A61B 1/041; A61B 1/00096
USPC .......................................................... 348/45
See application file for complete search history.

(56) References Cited

U.S. PATENT DOCUMENTS

| | | | | |
|---|---|---|---|---|
| 2010/0007896 | A1* | 1/2010 | Fishbaine | G01N 21/8806 356/603 |
| 2010/0046816 | A1* | 2/2010 | Igual-Munoz | G06K 9/6224 382/128 |
| 2011/0060189 | A1* | 3/2011 | Belson | A61B 5/4233 600/117 |

OTHER PUBLICATIONS

Rasouli et al, Wireless capsule endoscope for enhanced diagnostic inspection of gastrointestinal tract (Year: 2010).*

(Continued)

*Primary Examiner* — Shan E Elahi

(57) ABSTRACT

Disclosed herein are systems, methods, and structures providing accurate and easy to use size measurement of physiological features identified from endoscopic examination. In sharp contrast to the prior art, systems, methods, and structures according to the present disclosure employ structured light that advantageously enables size and/or distance information about lesions and/or other physiological features in a gastrointestinal (GI) tract. Advantageously, systems, methods, and structures according to the present disclosure are applicable to both capsule endoscopes and insertion endoscopes.

16 Claims, 21 Drawing Sheets

(56) References Cited

OTHER PUBLICATIONS

Itoh et al, A 2.6mW 2 fps QVGA CMOS one-chip wireless camera with digital image transmission function for capsule endoscope (Year: 2006).*

* cited by examiner

ENDOSCOPE EMPLOYING STRUCTURED LIGHT PROVIDING PHYSIOLOGICAL FEATURE SIZE MEASUREMENT

CROSS REFERENCE TO RELATED APPLICATIONS

This application is a continuing application of U.S. patent application Ser. No. 15/927,856 filed 21 Mar. 2018, which in turn is a continuation-in-part application of U.S. patent application Ser. No. 14/884,788 filed 16 Oct. 2015 now issued on 3 Apr. 2018 as U.S. Pat. No. 9,936,151, both of which are incorporated by reference as if set forth at length herein.

TECHNICAL FIELD

This disclosure relates generally to endoscopic examination of body lumens and more specifically to endoscopes and endoscopic examination employing structured light to facilitate the accurate dimensional measurement of lesions or other features observed during such examination.

BACKGROUND

As is known, endoscopes—including capsule endoscopes—allow clinicians to find and identify lesions and other physiological features in a gastrointestinal (GI) tract. Such capsule endoscopes are capsule shaped—having a tubular body with end structures giving them their capsule shape—and may advantageously be swallowed or taken into a stomach by traversing the throat and esophagus with a voluntary muscular action, as food, drink, or other substances. From the stomach, the capsule proceeds through the intestines and subsequently exits. Subsequent diagnosis oftentimes includes an estimation of the size of the lesion/feature since any health risk posed by the lesion/feature and any subsequent treatment regime(s) often depend on its size. For example, adenomas and sessile serrated polyps in a colon are typically categorized as advanced precancerous lesions if they measure more than 1 cm in diameter.

Despite the recognized importance of physiological feature size measurement, contemporary endoscopes—particularly capsule endoscopes—lack an accurate and easy to use method of size measurement for such physiological feature(s). Accordingly, methods, systems, and structures that provide or otherwise facilitate the size measurement of such physiological features identified from endoscopic examination would represent a welcome addition to the art.

SUMMARY

An advance in the art is made according to aspects of the present disclosure directed to methods, systems and structures providing accurate and easy to use size measurement of physiological features identified from endoscopic examination.

In sharp contrast to the prior art, systems, methods, and structures according to the present disclosure employ structured light that advantageously enables size and/or distance information about lesions and/or other physiological features in a gastrointestinal (GI) tract.

Advantageously, systems, methods and structures according to the present disclosure are applicable to both capsule endoscopes and insertion endoscopes.

Viewed from one aspect, the present disclosure is directed to endoscope systems including: a housing; at least one camera; a structured light source; and an array of microlenses that produces the structured light, the array of microlenses positioned such that light emitted from the structured light source is collimated by the microlenses into an array of beams propagating in multiple directions.

Viewed from another aspect, the present disclosure is directed to method(s) for imaging a body lumen comprising: introducing an imaging apparatus into the body lumen; emitting, from the imaging apparatus, non-structured light into the body lumen; detecting, by the imaging apparatus, non-structured light reflected from anatomical features in the body lumen; generating, by the imaging apparatus, one or more non-structured light images from the detected non-structured light; projecting structured light into the body lumen; detecting structured light reflected from the anatomical features in the body lumen; and generating one or more structured light images from the detected structured light.

BRIEF DESCRIPTION OF THE DRAWING

A more complete understanding of the present disclosure may be realized by reference to the accompanying drawing in which:

FIG. 6(A), and FIG. 6(B) are schematic diagrams showing illustrative microlens array (MLA) patterns in which: FIG. 6(A) shows a close packed (i.e., hexagonal or "honeycomb") arrangement and FIG. 6(B) shows a rectangular arrangement, both according to aspects of the present disclosure;

FIG. 9(A) structured light elements according to the present disclosure included in a contemporary insertion endoscope having structured light elements and additional white light elements according to aspects of the present disclosure; and FIG. 9(B) structured light elements according to the present disclosure included in an alternative contemporary insertion endoscope having a structured light channel and elements and additional illumination channel elements according to aspects of the present disclosure;

Figure 1:
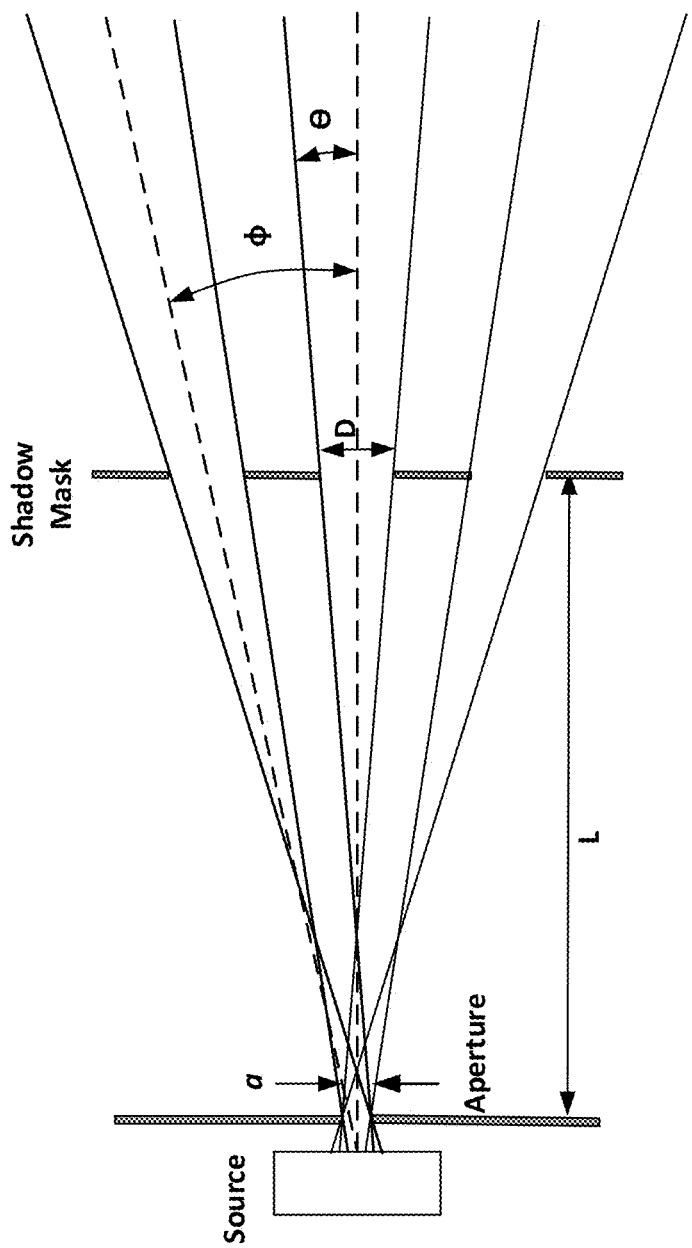
FIG. 1 is a schematic illustratively showing the generation of structured light with a shadow mask according to aspects of the present disclosure.

Illustrative embodiments are described more fully by the Figures and detailed Description. Embodiments according to this disclosure may, however, be embodied in various forms and are not limited to specific or illustrative embodiments described in the Drawing and detailed Description.

DESCRIPTION

The following merely illustrates the principles of the disclosure. It will thus be appreciated that those skilled in the art will be able to devise various arrangements which, although not explicitly described or shown herein, embody the principles of the disclosure and are included within its spirit and scope.

Furthermore, all examples and conditional language recited herein are principally intended expressly to be only for pedagogical purposes to aid the reader in understanding the principles of the disclosure and the concepts contributed by the inventor(s) to furthering the art and are to be construed as being without limitation to such specifically recited examples and conditions.

Moreover, all statements herein reciting principles, aspects, and embodiments of the disclosure, as well as specific examples thereof, are intended to encompass both structural and functional equivalents thereof. Additionally, it is intended that such equivalents include both currently known equivalents as well as equivalents developed in the future, i.e., any elements developed that perform the same function, regardless of structure.

Thus, for example, it will be appreciated by those skilled in the art that any block diagrams herein represent conceptual views of illustrative circuitry embodying the principles of the disclosure. Similarly, it will be appreciated that any flow charts, flow diagrams, state transition diagrams, pseudo code, and the like represent various processes which may be substantially represented in computer readable medium and so executed by a computer or processor, whether such computer or processor is explicitly shown.

The functions of the various elements shown in the Drawing, including any functional blocks labeled as "processors", may be provided using dedicated hardware as well as hardware capable of executing software in association with appropriate software. When provided by a processor, the functions may be provided by a single dedicated processor, by a single shared processor, or by a plurality of individual processors, some of which may be shared. Moreover, explicit use of the term "processor" or "controller" should not be construed to refer exclusively to hardware capable of executing software, and may implicitly include, without limitation, digital signal processor (DSP) hardware, network processor, application specific integrated circuit (ASIC), field programmable gate array (FPGA), read-only memory (ROM) for storing software, random access memory (RAM), and non-volatile storage. Other hardware, conventional and/or custom, may also be included.

Software modules, or simply modules which are implied to be software, may be represented herein as any combination of flowchart elements or other elements indicating performance of process steps and/or textual description. Such modules may be executed by hardware that is expressly or implicitly shown.

Unless otherwise explicitly specified herein, the FIGs comprising the drawing are not drawn to scale.

By way of some additional background, we again note that—despite the importance of measuring the size(s) of physiological feature(s) that may be identified from endoscopic examination—contemporary endoscopes—including capsule endoscopes—do not adequately provide such size measuring capability. Note that for brevity, we may interchangeably use the terms "features" or "lesion" to describe such physiological features. We note further that for the purposes of this disclosure and claims, such feature or lesion is simply an object or point of interest in a field of view and no nomenclature used herein is to be considered as limiting.

As will be known and readily understood by those skilled in the art, size measurement/estimation of an endoscopic camera image is error prone as the apparent size of an object or physiological feature to be measured depends upon its magnification, which in turn depends on its distance from the camera—which is generally not known. When an object is close to a camera, i.e., small conjugate distance, as is necessarily the case for in-vivo imaging, small changes in object distance produce large changes in magnification. Moreover, for the wide-angle lenses employed in endoscopes, lens distortion produces magnification variation across the camera field of view.

Those skilled in the art will readily appreciate that a tool (i.e., scale, forceps, or other object of a known size) of some sort may be used during an endoscopic examination as a size reference by positioning it sufficiently proximate to a lesion and viewing the tool and the lesion to provide a size reference to better estimate/determine the size of the lesion. As will be further appreciated, such a procedure may be time consuming, difficult or impossible for certain lesion positions in the bowel, not sufficiently accurate, present increased procedural risk of mucosal damage, and does not automatically record a measurement into a storage medium as part of the procedure record. Moreover, such tools are not available for capsule endoscopic procedures.

Of course, an endoscope including such tool that measures distance would enable a fast, simple, and objective measurement and recording of the size of objects in the gastrointestinal (GI) tract observed during endoscopic examination and would be a welcome addition to the art.

It is noted at this point that various electronic technologies have been developed for measuring the distance of objects, including radar, ultrasound, sonar, echo-location, lidar, holography, stereo-vision, depth-from-shading, time-of-flight, optical coherence tomography, confocal microscopy, and structured light. Many of these technologies require large, complicated, expensive, and power-hungry systems, methods, and structures. Optical time-of-flight measurements—including lidar—are challenging to employ for short object distance(s) because the time of flight is quite brief and therefore millimeter scale distance resolution is difficult to achieve. Optical coherence tomography (OCT) and confocal microscopy have been used in endoscopes and procedures employing same but are insufficiently miniaturized to provide utility for non-tethered, capsule endoscope applications. Finally, many of these noted technologies require sensor hardware that operates separately from optical white-light (WL) cameras employed by gastroenterologists or others (who employ endoscopes—i.e., endoscopists) to identify lesions and other features, making the correspondence between camera-image data and 3D-sensor data challenging.

Advantageously—and as will be readily appreciated by those skilled in the art and according to aspects of the present disclosure—3D data may be acquired by triangulation between an endoscope camera and a projector of structured light (SL). As will be further appreciated, such an approach leverages the camera—thereby reducing any extra hardware required and simplifying the establishment of a correspondence between white light image data and depth measurements.

As is used herein, structured light is spatially patterned so that an object space is illuminated with a pattern of known geometry in 3D space. Structured light involves a process of projecting a known pattern (oftentimes including grid or horizontal bar pattern elements, or random, pseudorandom, or semi-periodic elements) onto a scene (e.g., any field of view of an endoscope camera). The way(s) in which pattern elements deform when striking surfaces allows the determination of the depth and surface information of objects in the scene, as used by structured light 3D scanning systems. Advantageously, structured light may employ invisible (or imperceptible) structured light without interfering with other light-based vision systems and/or processes for which the projected pattern may be confusing. Illustrative invisible structured light includes the use of infrared light or of sufficiently high frame rates alternating between different patterns, i.e., opposite patterns.

By way of some specific examples, we note that structured light may employ an array of beams—emitted from one or more centers of projection (COP)—creating a grid of spots, lines, or other patterns on an illuminated surface. For triangulation, as will be known and understood by those skilled in the art, the COPs of the structured light projections must not be co-located with the COP of a camera imaging the pattern/surface.

Structured light may be generated by an image protector (structured light projector) that projects an image from a spatial light modulator or "slide" onto a surface. With respect to an in-vivo application, such surface may generally include biological materials including mucosa and/or lesions and/or other physiological features. However, optical efficiency of such image projectors decreases with the size of the system. For a single aperture image projector, flux is proportional to the focal-length squared. Since endoscopes typically exhibit a large field of view (FOV), e.g., 160°, it is difficult for image projectors to cover such a large FOV. Similarly, alternative technologies including miniature optical scanners using—for example—micro-electro-mechanical systems (MEMS) mirrors—cannot easily cover such a large FOV. Still alternative technologies such as diffraction gratings or holograms that operate by passing coherent light through a diffractive optical element (DOE)—while they may generate spatial patterns—such patterns however, only exhibit sufficient contrast in the diffraction far-field—typically at a distance of at least 1 cm from the DOE—and uniform coverage of a FOV exceeding 60° is difficult to achieve from a single source. Still another technological approach for generating structured light employing focusing lens(es) positioned at a focal length beyond the DOE produces images in the diffraction far-field at a distance equal to twice the focal length of the lens(es) from the DOE but results in a reduced coverage area (FOV) of the image.

Given these and other difficulties, the present disclosure is directed to systems, methods, and structures for the generation of structured light in a constrained spatial volume, exhibiting sufficiently low power consumption and low cost yet well suited for the illumination of object distances in the range of millimeters and beyond. As we shall show and describe, such systems, methods, and structures according to the present disclosure are particularly attractive to endoscopic applications and more particularly in-vivo capsule endoscopes. Notwithstanding such attractiveness, systems, methods, and structures according to the present disclosure advantageously exhibit applicability to other applications as well.

As will become apparent to those skilled in the art and for the purposes of presenting an elementary analogy, systems, methods, and structures according to the present disclosure employ a variation of a basic concept of casting shadows with a shadow mask. More particularly—and according to the present disclosure—light is passed through an array of apertures including micro-lenses that collimate the light into an array of beams—the intensity of which decreases less rapidly with distance than light passing through apertures without collimating lenses. Since each beam is independently collimated, the beam angles may vary widely to cover a larger FOV. Additionally, mirrors, lens(es), or other optical elements positioned beyond the micro-lenses may be employed to redirect some—or all—of the beams and increase FOV—as we shall show and describe in greater detail later in this disclosure.

At this point we note that those skilled in the art will readily understand and appreciate that a collimator is a device that narrows one or more beam(s) of light. As used herein, collimate means to narrow or cause direction(s) of light to become more aligned in a specific direction (i.e. that light rays describing the beam become more parallel), however, it does not mean that no divergence or convergence occurs in the collimated beam. It is possible that collimation may result in beams that have a smaller spatial cross section.

As will become further apparent to those skilled in the art, much of the disclosure presented herein is illustratively presented in the context of capsule endoscopes. The disclosure is not so limited. Systems, methods, and structures according to the present disclosure contemplate capsule and insertion-tube type endoscopes, as well as other instrumentation that may benefit from size and/or distance determination of objects of interest in a scene.

Turning now to FIG. 1, there is shown a schematic diagram of an illustrative apparatus generating structured light using a shadow mask according to aspects of the present disclosure. As may be observed from that figure, light is emitted from a source through an aperture (source aperture) having a diameter a. A shadow mask having an array of apertures (mask apertures) of width D is positioned a distance L from the source aperture through which the source light was emitted. Accordingly, and as shown illustratively in this figure, a divergence angle of light in a beam beyond the mask aperture(s)—ignoring diffraction on the axis with the source—is defined by:

$$\theta = \tan^{-1}((a+D)/2L).$$

As will be further appreciated by those skilled in the art, as the divergence angle increases, the greater the intensity of the light decreases with distance, thus requiring greater dynamic range in an image to adequately detect the presence and location of any projected patterns (spots, etc.) on both distant and near objects. As used herein and as generally understood by those skilled in the art, dynamic range describes a ratio between maximum and minimum measurable light intensities (e.g., black and white).

Reducing a and D (narrowing the mask apertures) reduces the divergence at the expense of throughput. Also, diffraction limits how much the divergence can be reduced by reducing D. Also, for projected spots to be distinguishable from neighboring spots, an aperture duty cycle of at least approximately 50% is required (i.e., the mask aperture pitch is at last 2D). Note that the shadow mask shown in the figure exhibiting square mask apertures must be substantially 50% opaque along axes in both lateral directions such that only approximately 25% of incident light striking the mask is passed. Such criteria are less for circular mask apertures.

Figure 2:
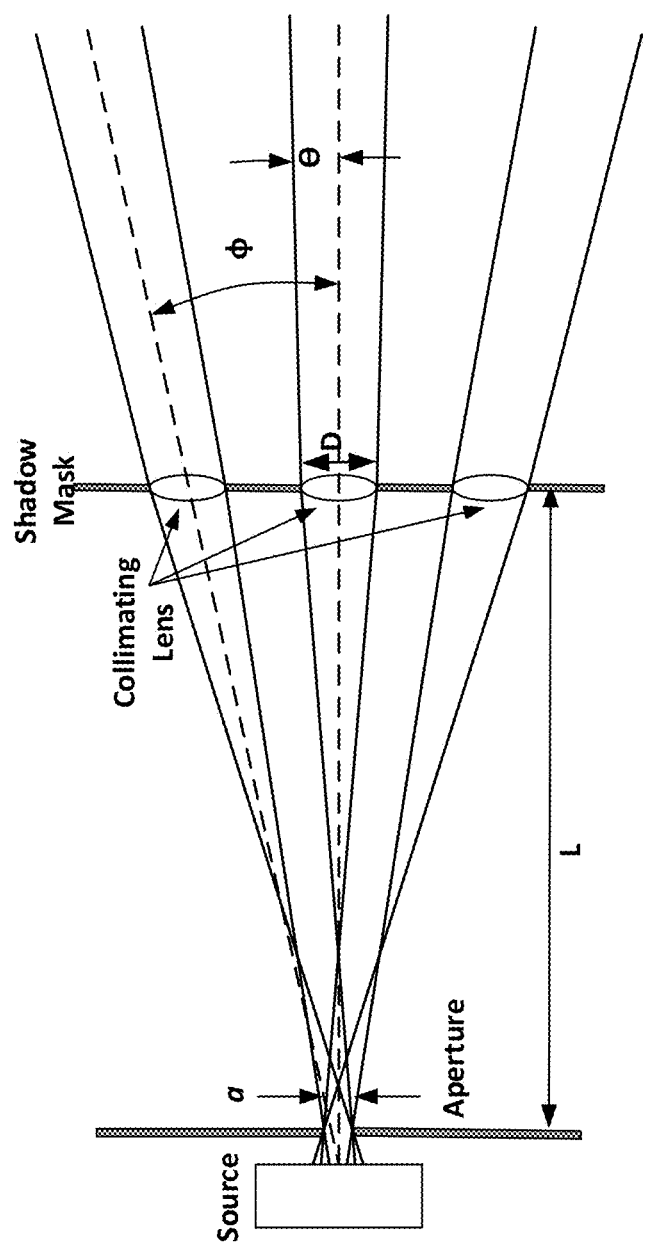
FIG. 2 is a schematic illustratively showing the generation of structured light with a shadow mask and collimating lenses according to aspects of the present disclosure.

With reference now to FIG. 2, there is shown a schematic diagram of an illustrative apparatus generating structured light using a shadow mask and a collimating lens positioned in each mask aperture according to further aspects of the present disclosure. If such collimating lens(es) are positioned in the mask aperture as shown, beam divergence—ignoring diffraction—is reduced to:

$$\theta = \tan^{-1}(a/2L).$$

While not yet specifically shown in the figures, a light source may advantageously include a "point-source" light-emitting diode (LED), which is an LED having a small aperture.

In an illustrative embodiment, a point-source LED exhibits a structure similar to that of a standard LED. However, the light emitted therefrom is emitted through a well-defined, (often circular) area, typically 25 μm~200 μm in diameter. The light so produced will appear as a "spot" producing a narrow viewing angle. As will be appreciated, such a point-source LED may eliminate or change the requirements of the source aperture (and any source mask having the source aperture) illustratively shown. (In such case, a is equivalent to an aperture diameter of the point source.) Typically, a lateral current-confinement structure is included in an LED such that an area in which electrons and holes recombine therein is not much larger than the aperture. The aperture may an opening in a metal layer on the surface of the LED.

Of course, a source employed in systems, structures, and methods according to the present disclosure may also comprise a laser, including a vertical-cavity surface-emitting laser (VCSEL) which may have an aperture of 10 μm or less, and is known to be much more efficient that a point-source LED. Unfortunately, if such a laser is highly coherent, the generated structured light may include spurious interference patterns and speckle noise.

Figure 3:
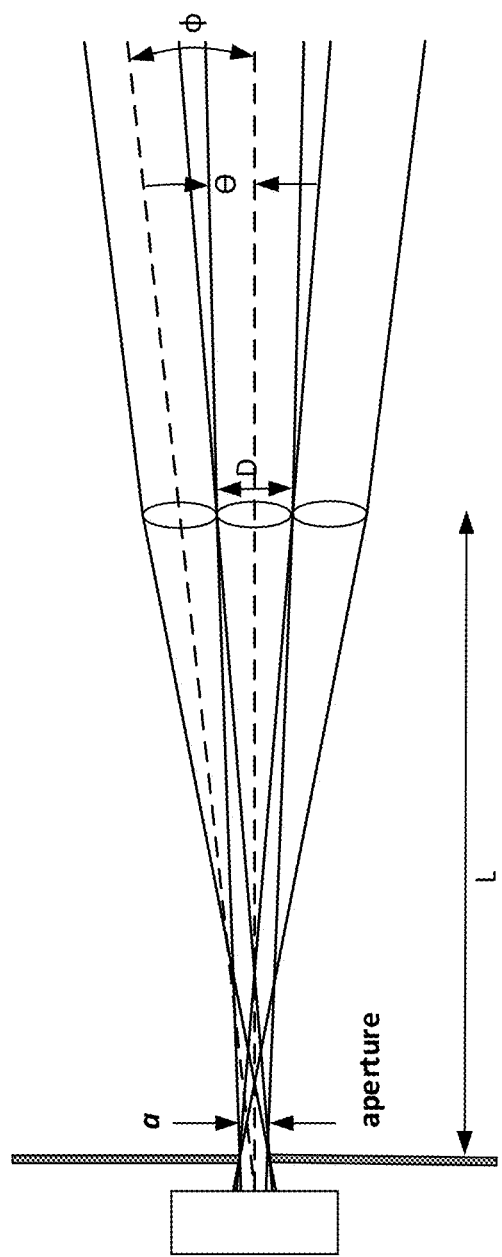
FIG. 3 is a schematic illustratively showing the generation of structured light with a shadow mask and collimating lenses according to aspects of the present disclosure in which the width of the apertures D is equal to the pitch (duty cycle is 100%)

For a point-source LED, a would typically be in the range of 0.050 mm to 0.20 mm (e.g., 0.080 mm or 0.10 mm) and L would typically be in the range of 1 mm to 10 mm. As such, for a=0.80 mm and L=4.0 mm, θ=6°. So long as D>a, the beam divergence θ is less than the beam separation angle ϕ and the duty cycle of any spots projected on an object decreases with object distance, even if the lens duty cycle is 100% (i.e., the pitch equals D). Such a configuration is shown schematically in FIG. 3. As will be appreciated by those skilled in the art, a large aperture duty cycle increases the throughput relative to a shadow mask having no collimating lenses.

Figure 4:
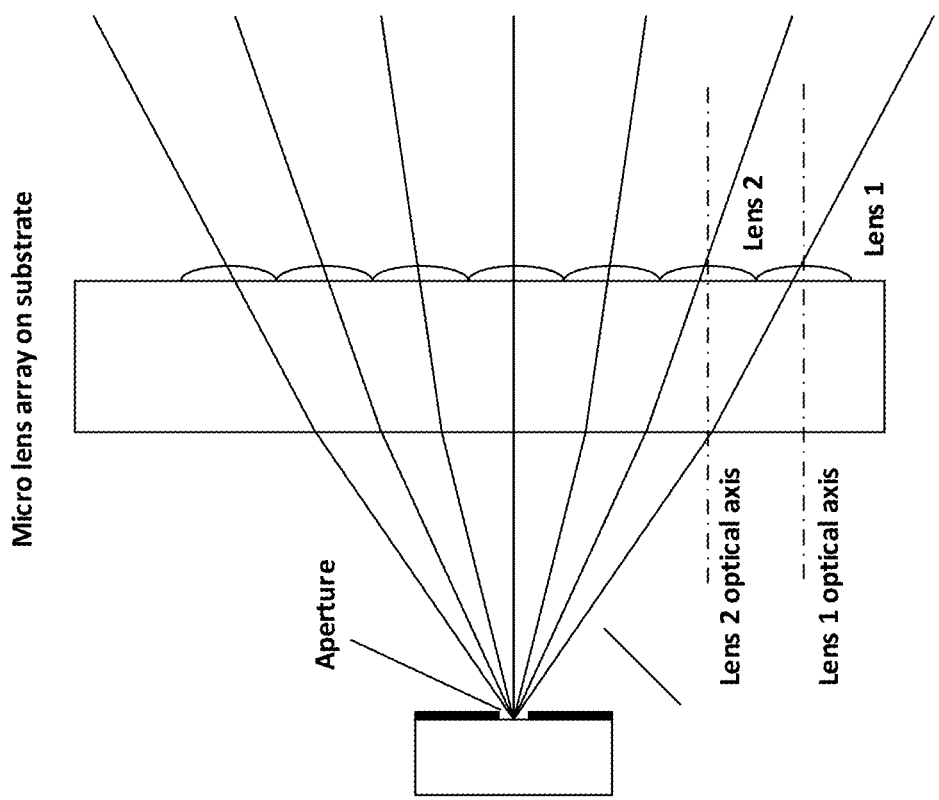
FIG. 4 is a schematic illustratively showing integration of a micro lens array (MLA) formed on/in a substrate according to aspects of the present disclosure.

At this point, note that a lens array such as that shown in the figures may be a micro lens array (MLA) formed or otherwise positioned on a transparent substrate. Such configuration is illustratively shown in the schematic diagram of FIG. 4.

With continued reference to that figure, it is noted that the substrate may be constructed from any of a variety of known materials including glass, silica, polymeric, or other transparent material(s). Likewise, lens(es) may be constructed from any suitable material and formed by embossing, molding, or lithography with photoresist reflow and/or etching or any other known technique. The lens array may reside on glass framework, which in turn may be affixed or otherwise integrated with the overall substrate. The lenses may be integrated onto the surface of the substrate facing the source or on the opposite side or integrated into the body of the substrate. Note that if the lenses are positioned on an opposite side of the substrate with respect to a light source, the focal lengths are larger for a same substrate position and thickness resulting in a reduced beam divergence.

Note further that each individual lens in the array has an optical axis—an axis of symmetry for the lens. For each lens, a chief ray passes from the source and intersects the optical axis at the lens entrance pupil. The chief ray and the optical axis lie in a tangential plane, and the chief ray also lies in a sagittal plane perpendicular to the tangential plane.

Figure 5:
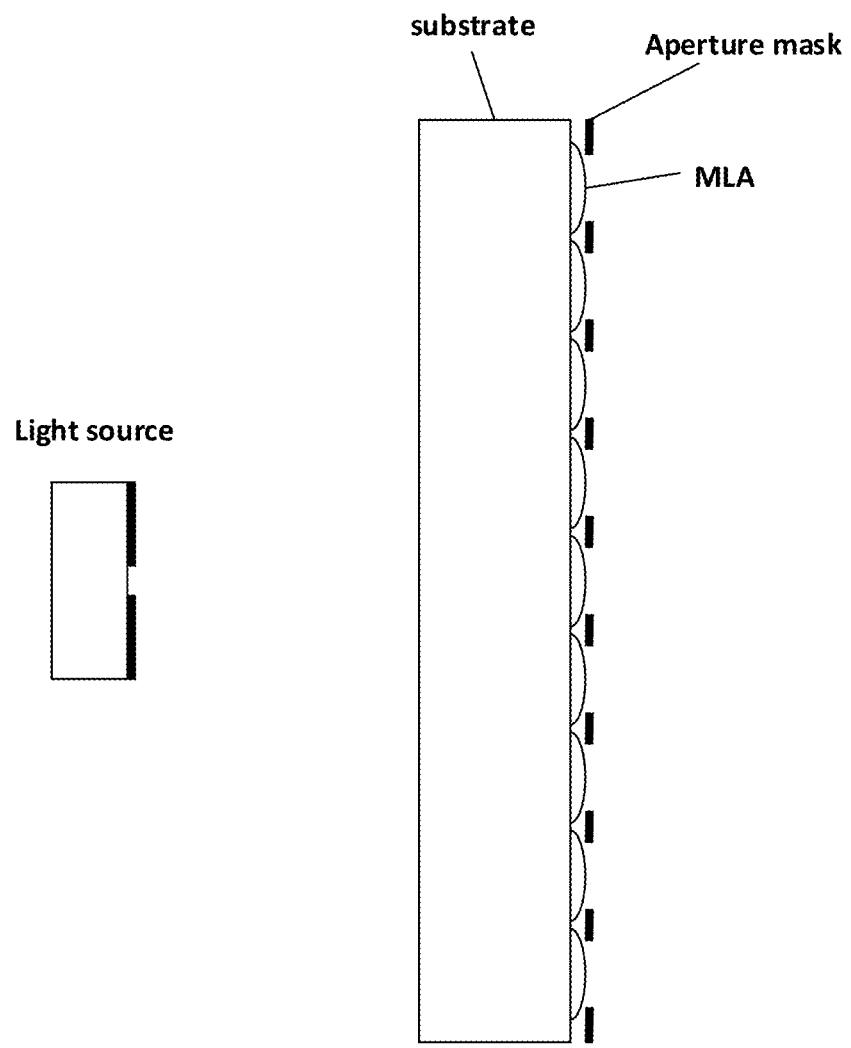
FIG. 5 is a schematic illustratively showing integration of a micro lens array (MLA) formed on/in a substrate with integrated aperture mask according to aspects of the present disclosure.
Figure 6:
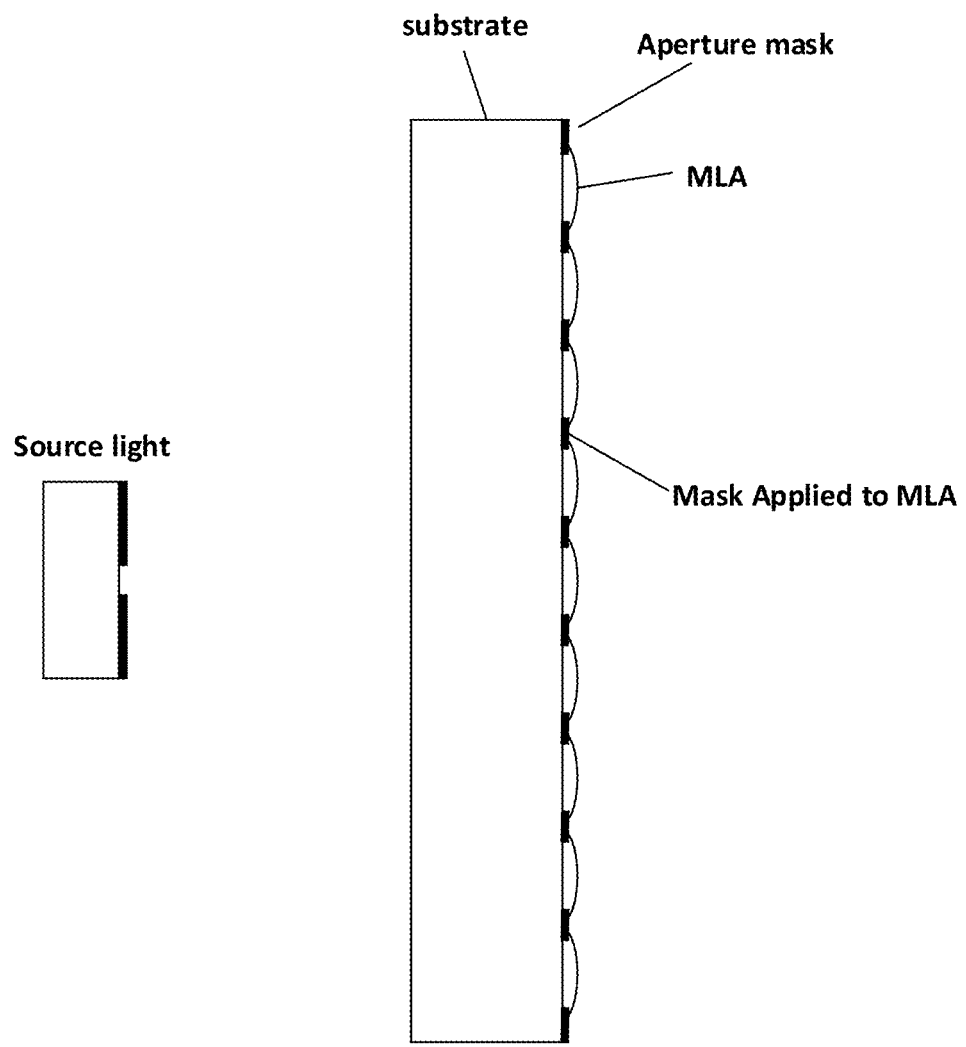
FIG. 6 is a schematic illustratively showing integration of a micro lens array (MLA) formed on/in a substrate and subsequently embossed/molded or etched to form the lenses according to aspects of the present disclosure.

With reference to FIG. 5, it may be observed that a surface of the lens material residing outside of lens clear apertures (CAs) may not exhibit a shape or quality (shape or otherwise) effective to collimate light with low aberrations. Advantageously, a mask may be employed to block any light that would otherwise traverse the MLA substrate outside of the CAs and reduce the contrast of the structured light projection—as shown schematically in FIG. 5. The mask may be constructed from a sheet of material or a coated substrate positioned immediately before or after the microlens array in the optical path depicted in the figure. Additionally, the mask may be an opaque coating applied to the surface of the MLA. For example, a black chrome or other opaque material may be deposited or otherwise applied on the surface of the lens array and patterned—using photo etching or other known methods—into apertures appropriately aligned with the individual lenses. Alternatively, black chrome or other opaque material may be applied and patterned on a glass substrate. Subsequently, a thin polymer layer may be applied to the substrate on the chrome (or other suitable material) and a mold applied resulting in an embossed lens pattern such that the lenses are aligned to the black chrome apertures. Illustrative structures resulting from such formation are shown schematically in FIG. 6.

Figure 6A:
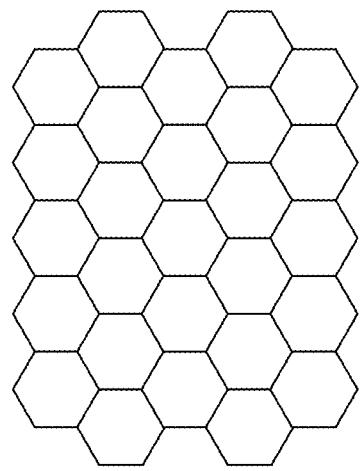
Figure 6B:
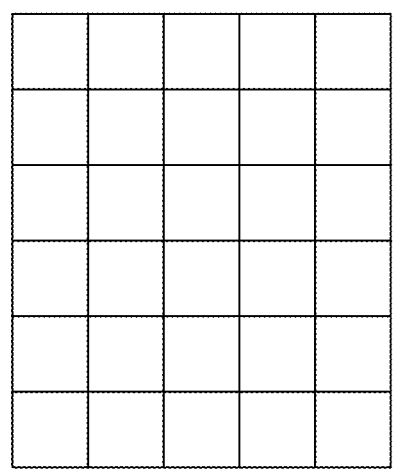

We note that microlenses may be configured in alternative arrangements (patterns) according to aspects of the present disclosure. For example, FIG. 6(A), and FIG. 6(B) are schematic diagrams showing illustrative microlens array (MLA) patterns in which: FIG. 6(A) shows a close packed (i.e., hexagonal or "honeycomb") arrangement and FIG. 6(B) shows a rectangular arrangement, both according to aspects of the present disclosure. As may be observed from those figures, these illustrative arrangements result in substantially no space between adjacent lens'—consequently a mask layer may be unnecessary for these arrangements. We note that in practice, however, the transition from one lens sag to the next adjacent one will not be perfectly sharp and therefore some light traversing through these transition regions will not be well collimated by the lens array. Notwithstanding such lack of collimation, a fraction of light so aberrated may be tolerably low so that no correction may be necessary.

With these MLA configurations in mind, we note the field-of-view half-angle covered by the structured light source is approximately $$\varphi \approx \sin^{-1}\left(\frac{w}{f}\right);$$

where w is the width of the MLA and f is the tangential focal length of the lens at the edge of the array. To minimize beam divergence, f, and hence the distance L from the source to the MLA, $\varphi$ should be as large as available space permits.

To increase FOV, w must be increased relative to f. However, the cost of MLA scales with its area and hence $w^2$. Also, as the angle of incidence for light through the MLA increases, lens aberrations, Fresnel losses, pupil distortion, and reduced light-emitting diode (LED) intensity (since LED intensity drops with angle) all become increasingly problematic.

Figure 7:
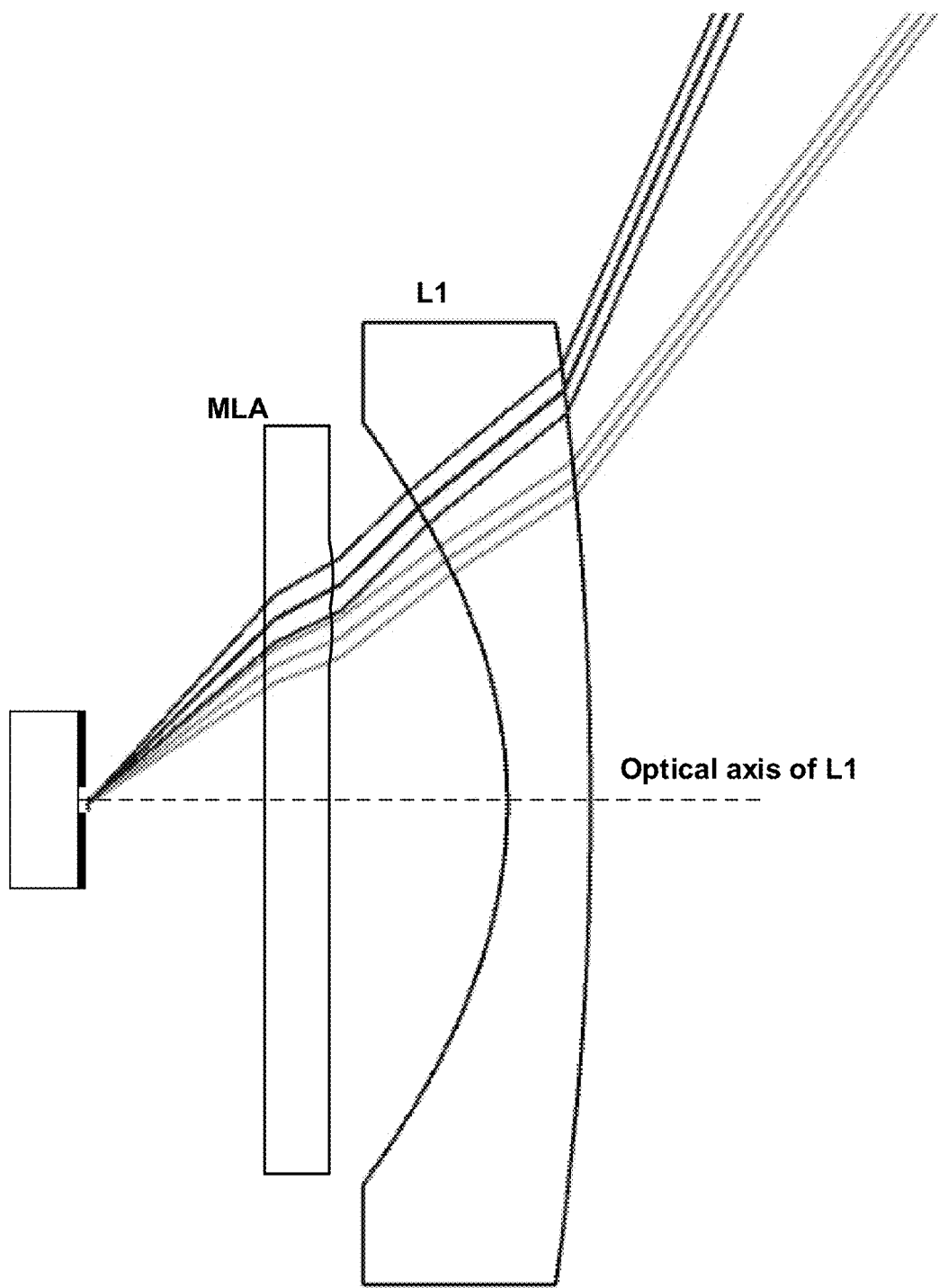
FIG. 7 is a schematic illustratively showing an optical element positioned after the MLA in the optical path such that overall field of view (FOV) is increased according to aspects of the present disclosure.

Advantageously, the FOV may be increased without increasing w/f by placing an optical element after the MLA which increases the divergence of transmitted beams. FIG. 7 is a schematic illustratively showing an optical element positioned after the MLA in the optical path such that overall field of view (FOV) is increased according to aspects of the present disclosure.

With reference now to that figure, there it shows a negative power refractive lens L1 positioned such that it follows the MLA in the optical path. In an illustrative configuration, a source is positioned on the optical axis of L1 and the lens array is perpendicular to this axis, but such arrangement advantageously need not be so exact.

As illustrated in that figure, rays are shown for two microlenses (MLs) of the MLA. Since L1 diverges the beams, the ML positive power is effectively increased such that they focus light from the source with finite conjugate to a point beyond L1. Additionally, the MLs exhibit different curvatures in the tangential and sagittal planes such that the beams in object space beyond L1 are approximately equally well collimated in both directions. Each ML collimates the light, making the rays that pass through it more parallel but somewhat convergent, and L1 further collimates the light, reducing or eliminating the convergence. Also, the ML curvatures vary with lens center position relative to the optical axis. To make beam widths substantially equal, the CA of MLs may increase with distance from the optical axis.

Additionally, a different type of optical element may be used in place of or in addition to L1 to increase the structured light (SL) FOV such as a Fresnel lens, a diffractive element, one or more mirrors, or one or more prisms. Finally, note that the FOV 2φ covered by the SL could be over 180°, or less than 180°, including—for example—160°, 140°, 120°, 100°, 80°, and 60°.

Figure 8:
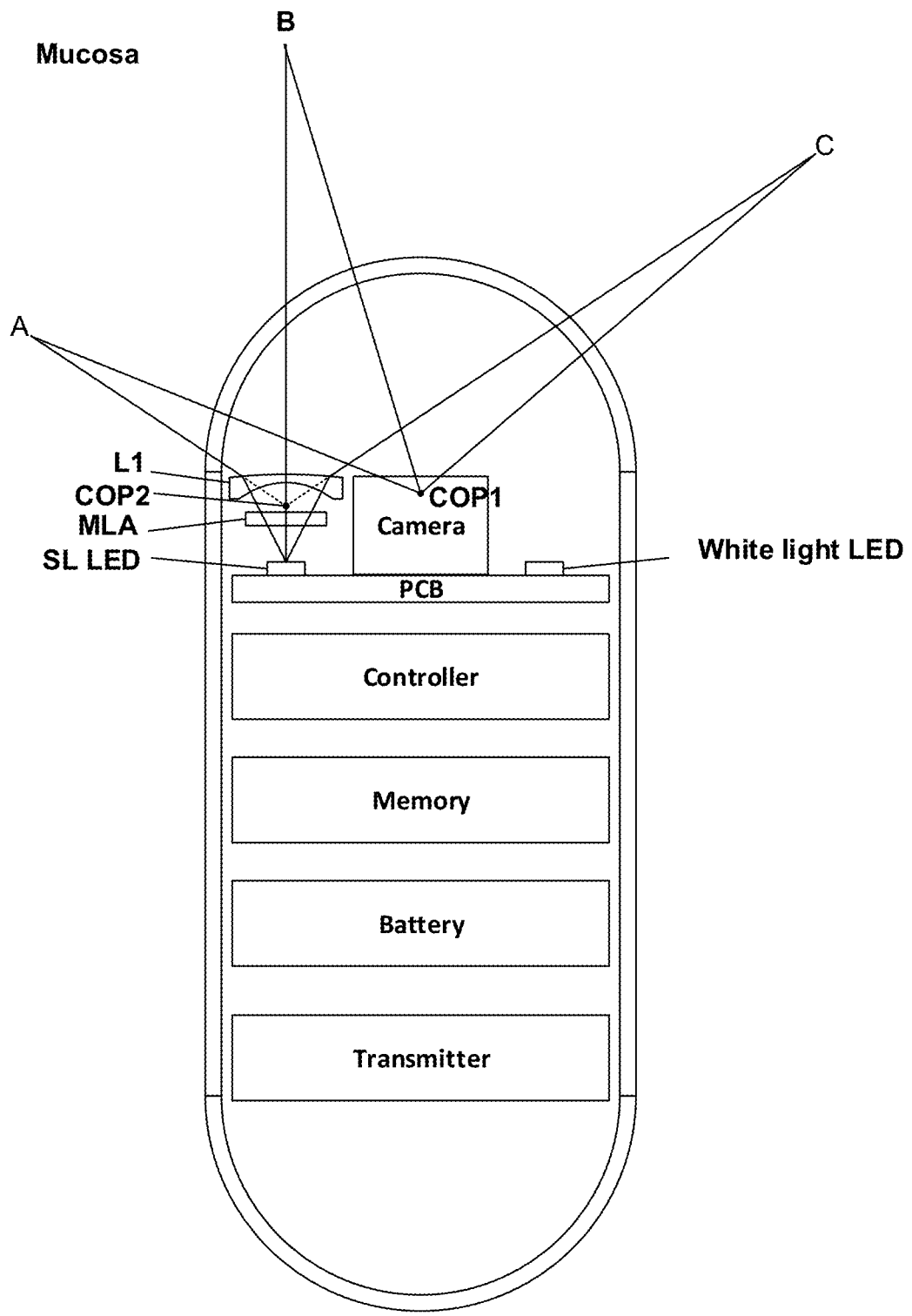
FIG. 8 is a schematic illustratively showing a capsule endoscope including structured light elements according to aspects of the present disclosure.

Turning now to FIG. 8, there is shown in schematic form an illustrative capsule endoscope including structured light elements according to aspects of the present disclosure. As depicted in that figure, a structured light source—which may include a light emitting diode or other suitable emitter/source including a laser—is positioned on a printed circuit board (PCB) and located within a body of the capsule. Shown in the figure, the structured light elements are positioned adjacent to a camera which—as will be readily appreciated by those skilled in the art—may generally include one or more sensors and/or imaging structures along with optical elements as well as any electronic and mechanical components. Note that many configuration possibilities are possible and contemplated by systems, methods, and structures according to the present disclosure in addition to those specifically shown in the figures. As an illustration, the camera and/or sensor may be mounted on the same PCB—or a different one—depending upon the particular configuration employed. Additional/other/alternative light sources may likewise be positioned around the camera.

For example, additional light sources may be placed around the camera in a ring or other arrangement. Additional structured light elements may likewise be positioned around the camera, and interposed between the light sources or, in any other arrangement that produces a desired illumination and structured light emissions and/or patterns.

As illustratively shown in FIG. 8, the capsule endoscope includes the structured light element having a structured light source (LED, or other light emitter—preferably point source), a microlens array and an additional optical element (lens) L1 shown illustratively exhibiting a negative optical power. Such a lens is advantageously positioned after the MLA thereby increasing the FOV coverage of the structured light element (SL projector/generator). Advantageously, L1 may be part of a molded (or other fabrication technique including 3D printing) structure that includes other functional optical elements and may extend at least part-way around the perimeter of the camera. Contemplated other functional optical elements that are not specifically shown in this illustrative schematic figure include other lenses, other/alternative SL sources and/or diffusers for additional/alternative light sources—including white light. Shown further in this illustrative figure the camera has a center of projection COP1 and the SL projector has a center of projection COP2—which is offset from COP1.

With continued reference to FIG. 8, it may be observed that the illustrative capsule endoscope includes a battery or other power source, a controller, memory, and a transmitter. The capsule itself includes a cylindrical body, with a dome-shaped window at one end and a dome-shaped body element at an opposite end. Note that while we have used the word "window" to describe the dome-shaped element forming/closing one end of the capsule body, such dome-shaped window may be made from any suitable material that is compatible with the cylindrical body and is sufficiently transparent to light employed. Note further that while the dome-shaped window is only shown at one end, contemplated configurations may include dome-shaped windows at both ends and duplicate/supplemental imaging systems/ structured light elements/optical elements may be positioned therein.

At this point we note that a capsule endoscope such as that according to the present disclosure is swallowable (ingestible) by a human and as such will exhibit a size of approximately 4 cm or less in length and approximately 2 cm or less in diameter. Such a capsule may be constructed from any of a number biocompatible materials that survive a trip through a digestive tract without comprising components contained within. Additionally, and as will be readily appreciated by those skilled in the art—at least portions of such capsules— in addition to exhibiting suitable biocompatibility—will also exhibit suitable optical properties. Once swallowed (ingested), capsules will pass through the digestive tract via physiological processes, including peristalsis.

As those skilled in the art will readily appreciate, additional hardware/electronic/optical components and additional software executed by the controller or other comparable structure(s) are contemplated. Operationally, image data stored in memory and then transmitted by the transmitter to external storage and/or processing systems. In certain illustrative embodiments, the memory may include longer-term, or archival storage in which image data is stored until the capsule is later retrieved after being excreted or otherwise removed from a patient. In yet other illustrative embodiments, the transmitter transmits data wirelessly through the patient body to an ex vivo receiver, for example, by radio, ultrasound, human-body electrical conduction, or optically. Advantageously, a general apparatus like that illustrated in FIG. 8 may be positioned on/within the tip of a traditional endoscope insertion tube rather than in a capsule endoscope as illustratively shown in FIG. 8. Such apparatus—as we shall show—may include combinations of those elements comprising the structure illustrated in the figure.

FIG. 9 is a schematic diagram showing an illustrative configuration of a contemporary insertion endoscope and insertion tube including structured light elements and additional white light elements and camera according to aspects of the present disclosure. As will be readily appreciated by those skilled in the art, the insertion tube will be passed through a body orifice or incision made therein. Once positioned inside the body, the camera system may capture images of an interior body lumen. Note that the illustrative structure shown in this figure is substantially the same as that shown earlier in FIG. 8. Of course, depending upon the particular endoscope design, various configurations of such an endoscope including structured light according to the present disclosure are well within the scope of this disclosure even where not specifically shown in this figure.

Figure 9A:
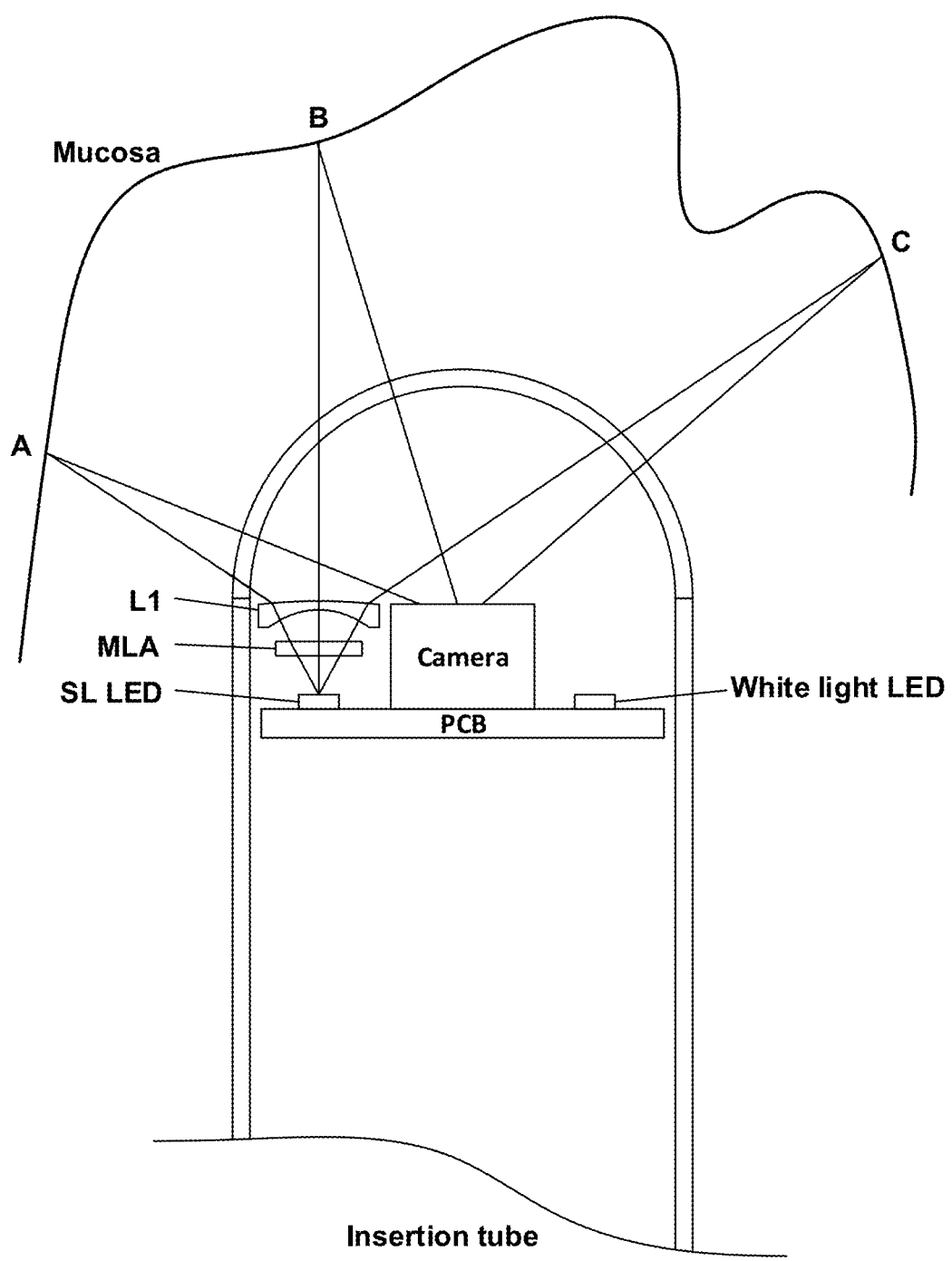
FIG. 9(A) and FIG. 9(B) are a schematic diagrams showing.
Figure 9B:
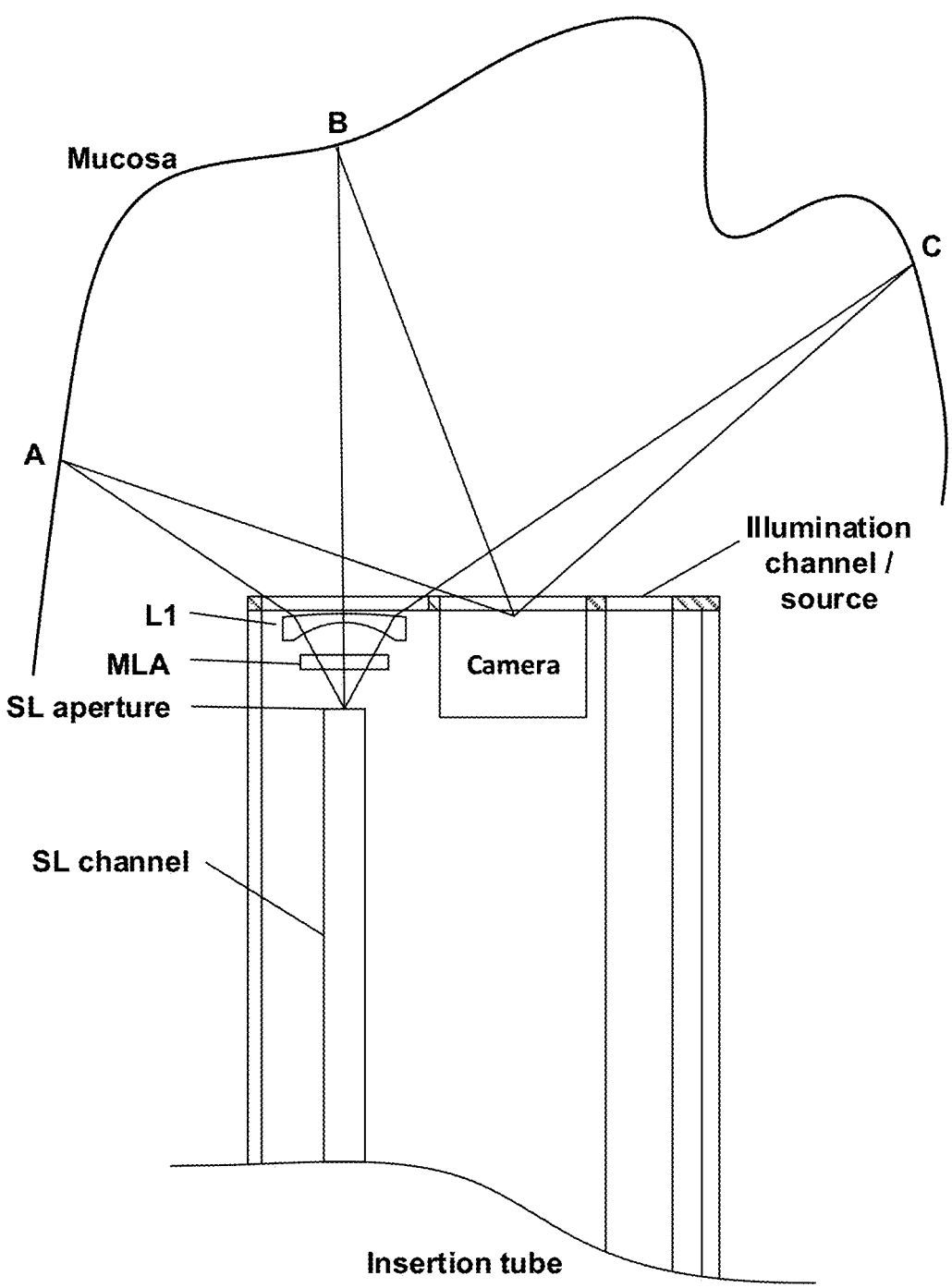

With simultaneous reference now to FIG. 8 and FIG. 9(A) and FIG. 9(B), we note that these figures illustrate three SL beam axes passing from the source, through the MLA, through lens L1 which deflects off-axis beams into larger angles thereby increasing the FOV, through the capsule housing and onto the mucosa (lumen wall) producing illuminated spots or patterns substantially centered at points A, B, and C in a cavity (lumen) of a human or other body. Light scattered from spots at points A, B, and C are collected and imaged in/by the camera.

Note that with reference to these three figures, systems, methods, and structures according to the present disclosure are shown in three different configurations—while sharing many aspects of this disclosure. FIG. 8 shows an illustrative capsule endoscope according to aspects of the present disclosure. FIG. 9(A) shows an illustrative insertion-tube-type endoscope according to aspects of the present disclosure, and FIG. 9(B) shows an illustrative insertion-type endoscope according to aspects of the present disclosure having a flat, non-domed end. Note further that with respect to the illustrative configuration shown in FIG. 9(B), the white, non-structured light is not generated at the distal end, rather it is generated elsewhere and conveyed to the end via an illumination channel. We note that such illumination channel/remote source may be replaced/supplemented by the LED or other source(s) disclosed. Likewise, the SL source is not shown in the distal end of the insertion tube. Rather the SL source is elsewhere, for example at or beyond the proximal end, and the SL is conveyed through the SL channel, such as an optical fiber or other lightguide, and emitted through an aperture (e.g. the end of the lightguide) and then passes through the MLA and L1. The SL source could instead be placed at the location of the SL aperture similarly to the example of FIG. 9(A), eliminating the need for the SL channel.

The white light source may be activated during an image sensor integration period of a same frame such that both SL and white light illuminate a captured image. Advantageously, the SL source may exhibit an optical spectrum that is different than that exhibited by the white light source such that it has a distinguishable color in images that include white light illumination. For example, the spectrum may be narrower such as that of a red, green, amber, or blue LED. The spectrum could—for example—fall outside the white light spectrum such as in the infrared (IR) region of the electromagnetic spectrum. Of course, an image sensor may include pixels with color filters that have a higher transmittance for the SL than for the white light. For example, pixels that are transmissive to IR and which absorb or otherwise block white light may be included on a sensor to advantageously detect IR structured light.

Figure 10A:
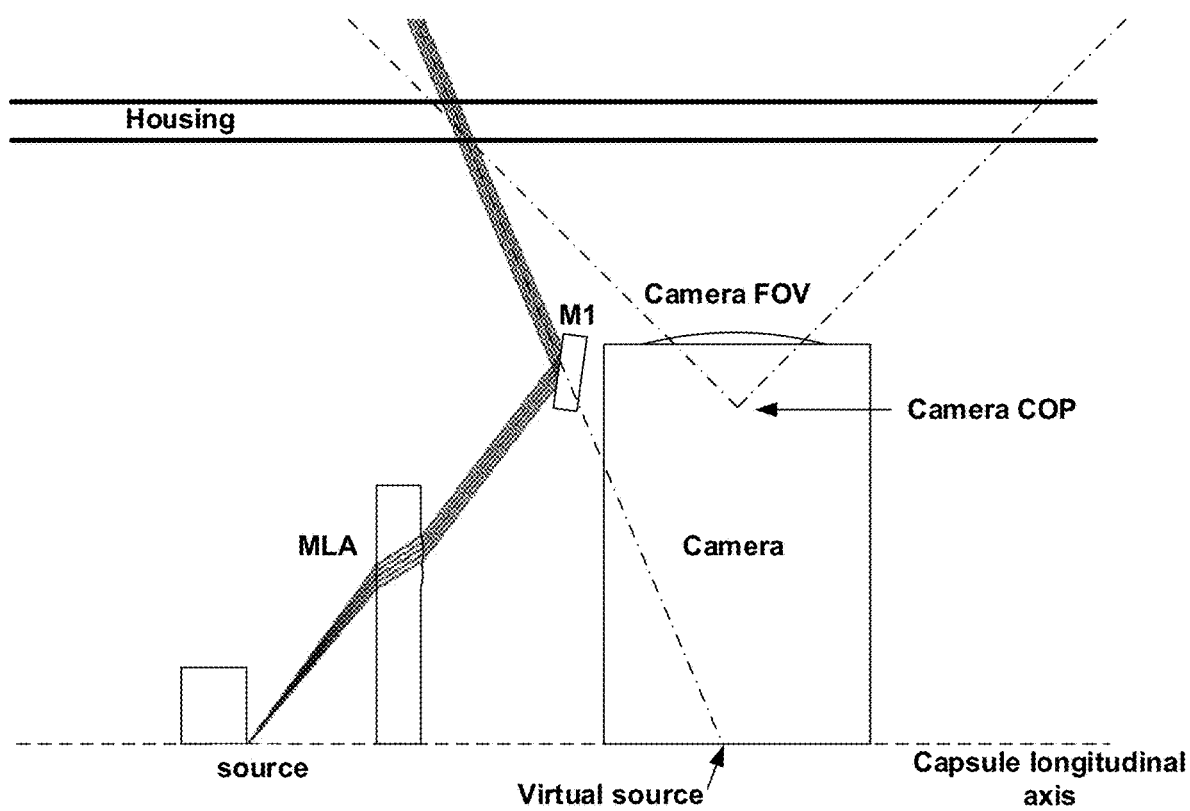
FIG. 10(A) and FIG. 10(B) are schematic diagrams illustratively showing a capsule endoscope including structured light elements and exhibiting a panoramic imaging system according to aspects of the present disclosure.
Figure 10B:
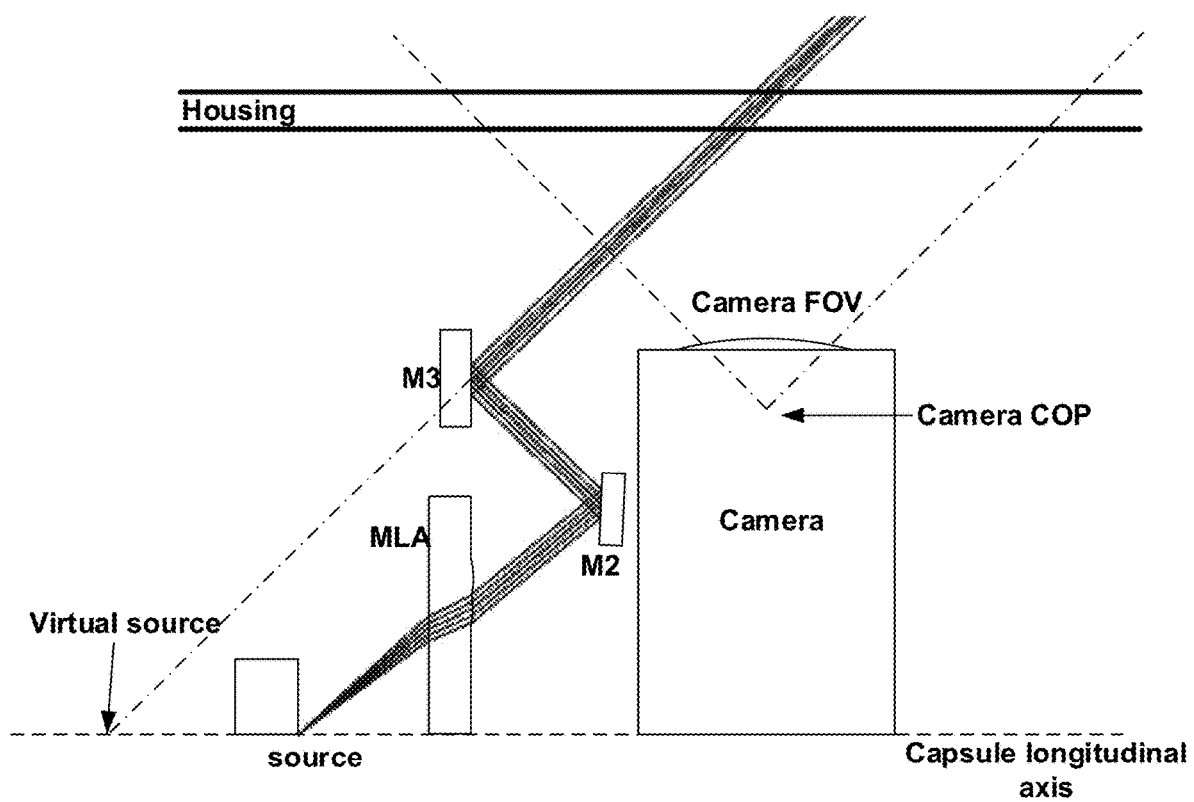

FIG. 10(A) and FIG. 10(B) show schematic diagrams of illustrative capsule section(s) (or specifically configured insertion-type endoscopes) including a panoramic imaging system and structured light elements. In these illustrative embodiments depicted, the panoramic imaging system may include—for example—four camera systems each facing the cylindrical—or tubular—wall of the capsule (or insertion endoscope). As will be readily appreciated by those skilled in the art—the actual number of camera systems employed in a particular configuration may be different from that shown in the figures namely, two, three, four, or more. Even a single camera system, typically including a panoramic imaging capability, would be useful in particular configurations.

Note that while FIG. 10(A) and FIG. 10(B) show cross sections of one side of an illustrative capsule, such capsules may advantageously exhibit a mirror-symmetry about a longitudinal axis so only one of four (in these examples) camera systems is illustrated. A point-source LED is shown positioned on or near the longitudinal axis of the capsule, displaced in the longitudinal direction from the camera.

Operationally, and as noted previously, light from the LED passes through a microlens array (MLA). In one illustrative embodiment, lenses comprising the MLA are centered on rings concentric with the LED, as shown illustratively in FIG. 11. As depicted in that figure, the lens array includes an opaque mask layer with apertures that block light incident on the array from the LED which is outside the Lens CAs.

Referring again to FIGS. 10(A) and 10(B), it may be observed (in FIG. 10(A)) the beam path for one lens of the MLA on one ring while in FIG. 10(B) it may be observed another beam path for another lens on another ring of the same MLA. In FIG. 10(A), the beams from one of the rings are deflected by mirror M1—which may advantageously be an annular mirror reflecting a set of beams, all of which pass through the same MLA ring. Note that M1 may advantageously exhibit a conical, spherical, aspherical or other shape as necessary.

As will be appreciated, mirror M1 directs (reflects) light beams out—through the tubular wall of the capsule housing. Relative to the axis of the light source—perpendicular to the MLA—M1 increases the angular field of view of the structured light beyond 180°. For example, the FOV may be 200°, 220°, or 240°. The mirror M1 reflection effectively "creates" a virtual source on the optical axis of the source that is shifted closer to the camera than the source. In FIG. 10(A), the optical axis of the source is shown as the longitudinal axis of the capsule.

To extract depth information from an image of the structured light captured by the camera system, the camera center of projection (COP) and the virtual source must be physically separated. As depicted in FIG. 10(A), the separation is more in the transverse direction than the longitudinal direction. Note that if multiple beams are deflected by M1 and M1 is symmetrical about the source, the virtual source corresponds to a COP of the SL projector.

Figure 11:
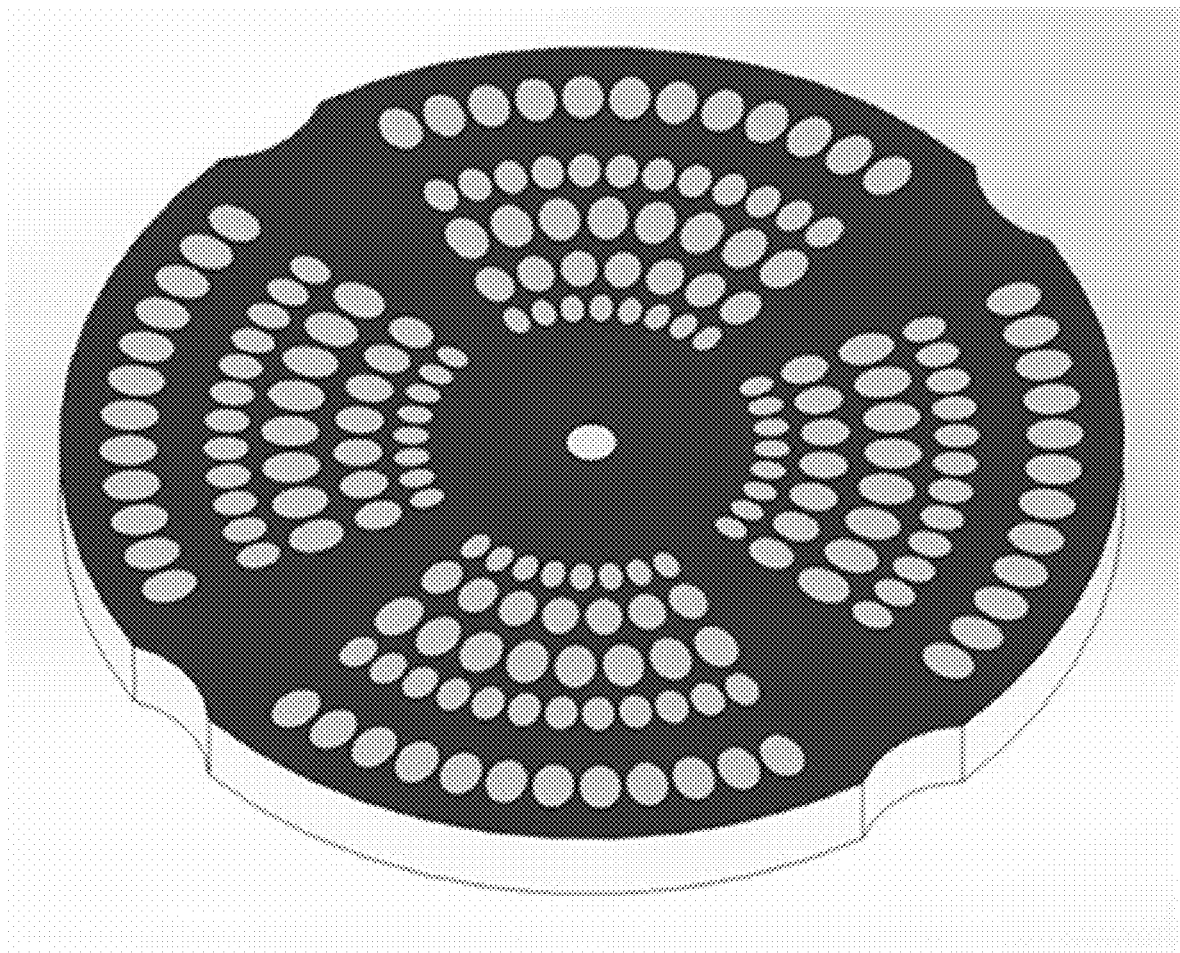
FIG. 11 is a schematic perspective view showing an illustrative MLA wherein microlenses of the array are arranged in concentric rings about a center LED according to aspects of the present disclosure.

Turning now to FIG. 11 there is shown a schematic diagram of an illustrative microlens array (MLA) in which the individual lenses of the array are arranged in substantially concentric circles. More specifically, the individual lenses are arranged on one of five, substantially concentric, circular rings. As configured in this illustrative arrangement, the rings are further arranged in four (4) distinct sections, azimuthally aligned to four side-facing cameras in a capsule (or alternatively, another endoscope or imaging device/structure including a single or multiple cameras with single or multiple imagers with at least one camera/imager associated with each individual section).

Note that the lens CAs are defined by a patterned black opaque layer of material such as black chrome. The clear(er) apertures are shown as being elliptical—although they could be other shapes including circular or rectangular—among others. The long axis of the oblong lenses lies in approximately tangential planes. The projection of the aperture onto a plane perpendicular to the chief ray is foreshortened. The oblong aperture compensates for the foreshortening to produce a more symmetrical beam. Larger apertures pass more light than smaller apertures so that the relative intensity of the beams is controlled by setting the aperture sizes.

At this point we note that the optical systems depicted illustratively in FIGS. 10(A), 10(B) and FIG. 11 are symmetrical—or approximately symmetrical—about the center of the system (e.g., capsule). However, as those skilled in the art will readily appreciate that such "center symmetry" is not necessary. For example, one or more sources may be configured such that they are centered off the longitudinal axis. Additionally, and/or alternatively, mirrors M1, M2, and M3 may not exhibit a rotational symmetry about the longitudinal axis and the lenses in the MLA may not lie on circular rings. For a capsule system having four cameras, it may be advantageous to implement four separate SL systems—one for each camera. The four systems may advantageously employ a common MLA substrate.

Returning our discussion of FIG. 10(B), it may be observed from that figure that a lens in the MLA reduces the divergence of light emitted by the source and a mask layer (not specifically shown) filters light outside of the lens CAs. The one beam shown is representative of all beams passing through one ring of the MLA. The beam is deflected by mirror M2 and then again by mirror M3. As will be readily appreciated, mirror M2 and mirror M3 may be annular mirrors.

As illustratively configured, the radial position of M2 inside the capsule is less than that of M1 and the mirror apertures do not overlap such that both M1 and M2 may exist in the same system. After reflection from M3, the beam passes out through the tubular wall of the capsule and illuminates mucosa within the field of view of the camera. The combination of M2 and M3 reflections results in a beam angle exiting the housing similarly to the angle upon exiting the MLA.

As may be observed, however, the beam is displaced and appears to emanate from a virtual source (center of projection) further from the camera than the source on the longitudinal axis. Light emitted directly from the MLA would have been blocked by the camera and therefore prevented from exiting the capsule. By moving the virtual source further from the camera than the source, the beam passes the camera without being blocked. As will be readily appreciated by those skilled in the art, this same approach may be employed to route beams around other obstacles. Note that since during normal operation mucosa will contact the capsule housing—it is desirable to position mirrors to direct the light beams to cover as much of the housing within the FOV as possible.

Figure 12:
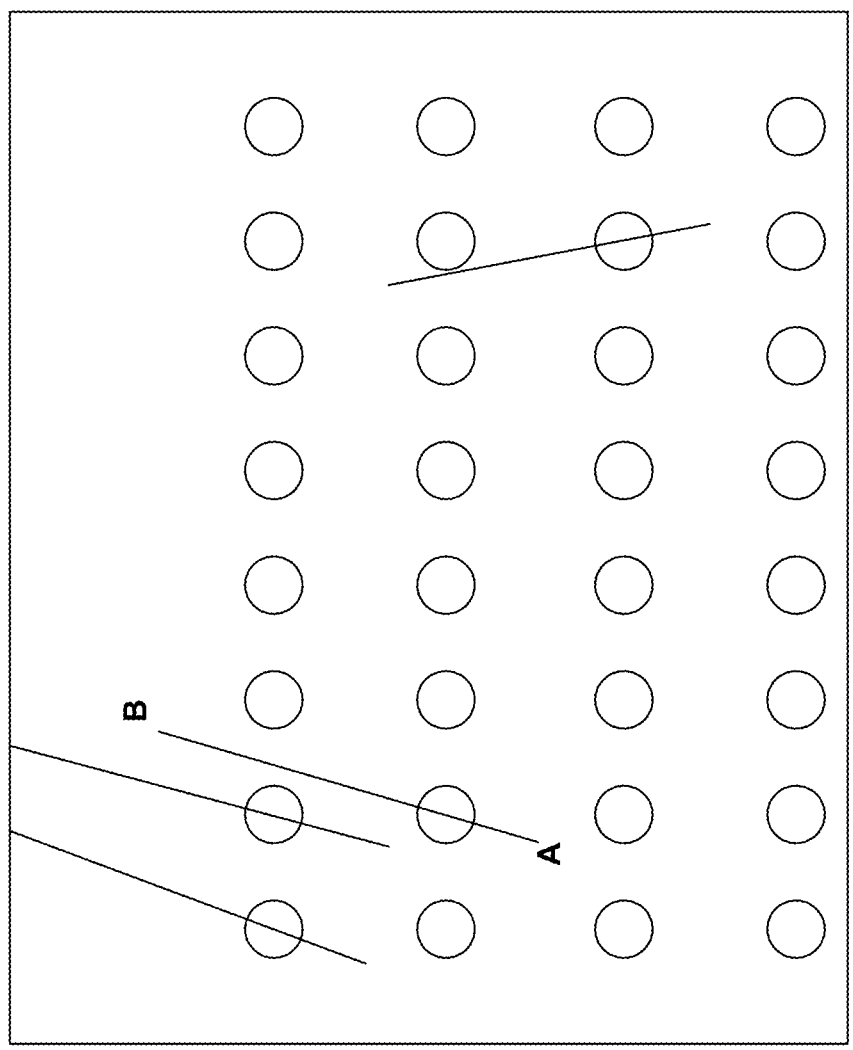
FIG. 12 is a schematic diagram illustrating an image captured by a camera—configured according to the present disclosure—the image being of a planar surface with SL projected onto it according to aspects of the present disclosure.

FIG. 12 is a schematic diagram illustrating an image captured by a camera—configured according to the present disclosure—the image being of a planar surface with SL projected onto it. The spots are produced by the intersection of SL beams with an object plane. Each SL beam is illustratively produced by a microlens of the MLA. As the object moves further from the camera, the spot centroids move on converging epipolar lines, four of which are illustrated in the figure.

For example, one spot is at point A if the object is contacting the endoscope and at point B if the object is at the edge of the system's useful range. Each spot moves on its own epipolar line (or curve, if the camera image is distorted). To extract depth information about points in the scene, the system identifies spots in the image and determines a correspondence between the spots and the epipolar lines, which are based on a camera model. The correspondence may be confounded if epipolar lines cross and a spot is detected near an intersection. Fortunately, standard, known techniques exist for resolving this and other ambiguities to establish the correspondence for all or most of the spots.

In particular, the position of each spot on its epipolar line is determined and this position establishes the depth of the object at the spot location in the image. The greater the number of spots, the better the resolution of the depth map that is determined. Since the size and brightness of the spots also decrease with object distance—these quantities may also be used to determine the distance of the object(s) onto which the spots are projected. Rather than identifying a correspondence between individual spots and epipolar lines, the shape of a surface with structured light projected thereon may be estimated by other known methods such as determining the SL pattern deformation by determining correlations between portions, comprising multiple spots, of the projected and imaged pattern with portions of the known undeformed pattern to determine a map of the pattern deformation from projection on the surface.

While not yet specifically shown in the figures, it is nevertheless noted that an endoscope system according to the present disclosure will generally include one or more computers (or equivalent systems/structures/functionality) to receive image data from the endoscope system, process the data, display image data to a human—or "display" to an expert system—receive inputs from the human/expert system via an interface (e.g., GUI), present analysis results such as estimated object size, create or update a database of procedure data, and generate reports of the medical examination results.

The images—which include SL—are analyzed to extract information about the distance of objects visualized in the images. This analysis may advantageously be performed in a batch mode for many or all SL images prior to presentation to a human reader or, to reduce processing time, it may be performed on select images that are flagged or otherwise identified by the reader or machine (e.g. expert system/ algorithm(s)) that operate on a set of images to determine images of interest. For example, either a reader or machine (algorithm) might identify a possible lesion in a particular frame, and then the depth information for that frame and/or neighboring frames is extracted from the structured light image data.

We note that endoscope images are typically presented to a reader as a series of still images such as a video. The reader views the video looking for pathologies or other objects of interest. Frames containing such objects (frames of interest) may be selected and placed into a list or database of selected frames for the particular medical procedure.

As will be appreciated, some frames may include objects or regions within the overall image for which the reader desires a size measurement. Such measurement may then be operationally indicated by the reader by any of a number of well-known computational tools including GUIs. For example, the reader may select points on a periphery of a region, draw a curve around periphery or draw a line across the region.

The system will then estimate the distance across the indicated region, for example between two designated points. If the image includes structured light, it may be used to estimate the distance in object space of any objects/ features of interest in the image. From the structured light, a 3D model of a scene or portion of a scene—represented by the image—may be constructed. Such model may be coarse if the density of SL points is significantly less than the pixel density of the image.

While direct depth information may be available for those pixels that lie near the centroids of the SL spots, it will not be for pixels that lie between spots. As may be understood and readily appreciated by those skilled in the art, additional information in the image such as detected edges or depth-from-shading may be used to better estimate the depth information across the image. Advantageously, the depth may also be estimated in regions between the SL spots by interpolation from the calculated depth at the SL centroids. Once the 3D coordinates for two or more points demarcating an object are estimated, the cartesian distance between them in object space is determined.

A size measurement is typically displayed to a reader and recorded in a database. The functions of identifying and demarcating a region of interest may be performed by a machine-executed algorithm instead of a human reader, or the reader may work in conjunction with such machine-executed algorithm(s) to identify and demarcate such regions.

As will be readily appreciated by those skilled in the art, if structured light (SL) and white light (WL) illumination exist in the same frame, a system must identify the structured light within a regular WL image background. Note that scattered SL may also produce background light. Note further that the structured light spots are known to line on epipolar lines. The location of these lines is determined from a camera model that may be based—at least partially—on camera and projector calibration. More particularly, the system looks for image features that best match the structured light in an expected shape, size, intensity, and color. Color—in particular—provides a useful way of distinguishing SL from WL when such SL color is sufficiently different from the WL illumination color.

We note that when reviewing a video or other set of images captured from an endoscopic system according the present disclosure, visible structured light in the video (or images) may be a distraction to the reviewer. Accordingly, various methods may be utilized to remove it from an image once such SL spots are identified.

More particularly, an estimate of an SL pixel signal may be subtracted from the image. Such estimate may be based on a model of the SL including its color. Accordingly, if a particular pixel is saturated in a color plane due to the SL or if the SL signal to be subtracted is large, then the white light image signal in that color plane may be estimated based on the signal in other color planes.

For example, if the SL is predominately red, the red color plane may be reconstructed from the green and blue color plane data for pixels within the SL spot based on a statistical correlation between red, green, and blue color planes in the region of an image around that spot. Methods such as "in painting" may also be used to fill in missing image and create a continuous image appearance. To eliminate chroma error—resulting from imperfect SL subtraction from the image—it may be advantageously displayed as a gray-scale image. If the structured light is in the IR and the structured light is detected by IR pixels, then an RGB image with minimal impairment by structured light is available.

Note that methods employed to subtract the SL from images are likely to leave some residual impact on the image quality. Therefore, it is desirable for the SL to be captured in separate frames from the white light frames. As will be understood, the time difference(s) (separation) between the white light and SL frame(s) should be short enough such that any change in scene is sufficiently small that depth information determined in the SL frame(s) may be applied to the scene(s) in the WL frame(s) with minimal error.

To reduce the impact of any scene, change(s), the reviewer/reader may demarcate an object in two or more WL frames. Then, the position and size—in pixels—of the object in a SL frame temporally positioned between two WL frames (i.e., interstitial) may be estimated by interpolation between the WL frames. If the object of interest appears in multiple frames, then the reviewer/reader (or machine system/algorithm) may select one or more frames in which to demarcate the object and a proximal SL frame in which to estimate the object size—based on an estimate of a rate of object movement—selecting frames with minimal—or acceptable—movement. We note that the amount of movement of objects in a video or series of images may be estimated by known methods such as the calculation of motion vectors. The motion metric on which frames may be selected may be based more on the motion of the particular object region to be measured in the video than the overall motion of the entire scene.

Advantageously, a reviewer/reader or image recognition system algorithm (including any employing machine learning methodologies) may identify an object in one frame that is of interest. Then, the reviewer—or system—may search for the same object in neighboring frames using pattern recognition methods and/or algorithms. Then, from the set of frames including the object, one or more frames may be selected for object-of-interest demarcation.

The frames may be selected based on multiple criteria such as a rate of object movement, the fraction of the object within an image boundary, and the quality of an image including factors such as exposure, motion blur, obscuration by fecal—or other—matter, and the presence of bubbles or turbidity. The algorithm may select particular frames and the reviewer/reader may confirm their suitability by making an entry using the GUI or other mechanism. In illustrative embodiments, selected frames may have check boxes that are selected to keep or deselect frames. The demarcation of the object in these frames may advantageously be performed manually using—for example—the GUI—or other mechanism—by the reviewer/reader or automatically by a system with confirmation or fine-tuning by the reviewer/reader. The size measurement based on the demarcation and analysis of SL in the same or proximal frames may be presented to a reviewer/reader on a screen. The measurement presentation may include—for example—error bars, confidence intervals, or other indicators of the accuracy of the measurement.

As will be readily appreciated by those skilled in the art, a video—or series of images—captured by a capsule endoscope moving autonomously through a GI tract has many image frames exhibiting redundant information since at times the capsule is not moving, moves retrograde, or dithers. The endoscope system may not display some frames that are determined to be redundant, i.e., showing the same features that are displayed in other frames. Also, multiple frames that capture overlapping images of the scene may be stitched into a composite image. As will be understood, this reduction in frame number reduces the time needed to review the video.

When an object of interest—such as a lesion—is identified in one of the displayed frames the system may display a version of the video with all frames displayed—including those previously not displayed or those combined with other frames into stitched frames. The process of finding optimal frames in which to demarcate the object and measure its size, as described previously, can be applied to this larger set of frames. The best frame(s) for demarcating the object—based on criteria described above, or others—may be one of the frames that was not originally displayed.

Note that a region of interest for size measurement may not be fully visualized in a frame, especially if the region is large. However, two or more frames containing portions of the region may be stitched together so that all or most of the region is captured in the stitched frame. The region may be demarcated in the stitched frame and cartesian distance between demarcation points may be estimated based on the structured light data in the frames stitched and/or interstitial frames.

As will be appreciated by those skilled in the art, capsule endoscopes present some particularly unique imaging conditions. Accordingly, the magnification of objects imaged by an endoscope camera (whether a capsule or insertable) is larger if the object is immersed in a fluid rather than in air or other gas. Thus, the correct estimation of object depth using structured light depends on a knowledge of the immersing medium.

During a colonoscopy, the colon is insufflated with gas. For capsule endoscopy, the colon and other organs are preferably filled with clear (colorless) water. However, gas bubbles, including large pockets of gas, do exist in the lumen during capsule endoscopy. In a video or set of images, these bubbles may be recognized due to the appearance of bright specular reflections of the illuminating light from the wet mucosal surface and a change in mucosal color, relative to water immersed mucosa. Moreover, a meniscus is visible where the bubble boundary crosses the capsule housing.

When a reviewer/reader or a machine algorithm has identified an object for size measurement, the reviewer may be queried to determine whether the object is immersed in a liquid or a gas. Since the object may be partially in a liquid and partially in a gas, the reviewer/reader may indicate a gas/liquid ratio for the immersion or may use a cursor tool (or other GUI or other mechanism) to mark areas that are in gas or in liquid. Of course, a computer implemented method/algorithm may perform these same functions.

The geometric model of the SL is modified based on the medium selected. Alternatively, a measurement based on a fixed single-medium model may be scaled ad hoc based on the selected medium. For example, if the SL model assumes water immersion, but a fraction P of the diameter of a measured object is in gas (e.g., P=0.40), the size estimate may be adjusted by PM where M is the relative magnification in gas versus liquid. Finally, M may be a function of field position and estimated object distance and may be based on an a-priori camera model and calibration.

At this point we note that endoscope calibration may advantageously be performed during manufacturing. More particularly, an endoscope may be presented with targets at known positions and orientations relative to the endoscope camera. Some targets may include a pattern such as a checkerboard. The location of the features in the pattern in the recorded image can help determine a model of the camera including focal length, COP, pose, and distortion. Other calibration images are formed by illuminating SL from the endoscope onto one or more targets. These calibration images help determine a model of the SL projection including COPs, pose, epipolar lines, and color.

Note that for a capsule endoscope, it is convenient to store calibration data as well as any images and/or parameters derived from images, in a capsule endoscope memory. This data can then be downloaded with any in vivo data to a workstation for processing the in vivo data and extracting depth information from in vivo images using camera and SL models derived from—at least partially—the calibration data. Alternatively, the calibration data for a capsule can be associated with a capsule identifier, such as a serial number, and be stored in a database. Upon recovering the in vivo data and the identifier from the capsule, the calibration data associated with the identifier can be retrieved from the database and use for processing the in vivo data.

Figure 13:
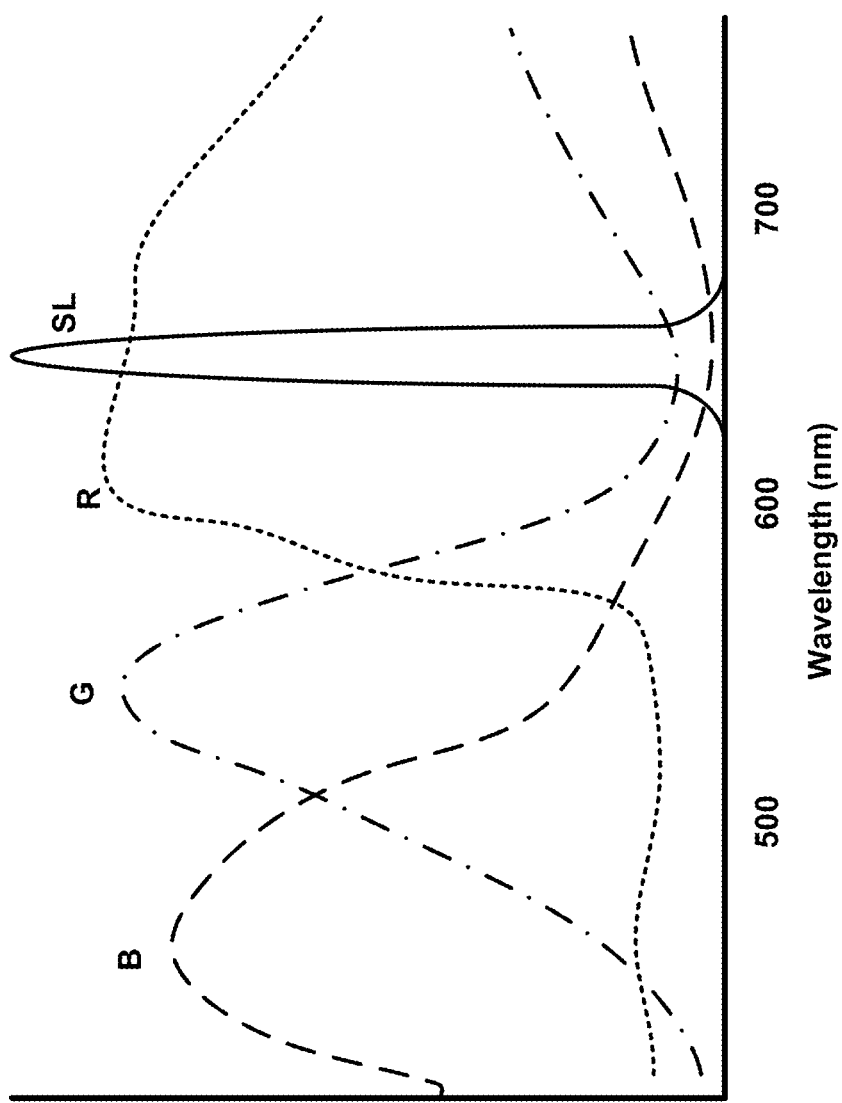
FIG. 13 is a plot illustrating a responsivity spectrum for an illustrative sensor and the emission spectrum of an illustrative structured light source included in an endoscope structure according to aspects of the present disclosure.

Image sensors used in endoscopes oftentimes include a mosaic of color filters on the pixels. For example, a sensor may have red (R), green (G), and blue (B) pixels with responsivity spectra as illustratively shown in FIG. 13. The SL spectrum is shown with center wavelength of 650 nm. Over the bandwidth of the SL, the R pixels have the largest responsivity, followed by G and then B.

Operationally, when SL illuminates mucosa, some light is scattered from the surface of the mucosa and some light penetrates the mucosa tissues and experiences a combination of absorption and bulk scattering. Some of the bulk scattered light emerges from the mucosa some distance from the point of incidence. The visible SL spot is thus spatially broader than the light incident on the mucosa due to the diffusion of light in the tissues. This broadening or blooming could make it difficult to distinguish one spot from another.

Figure 14A:
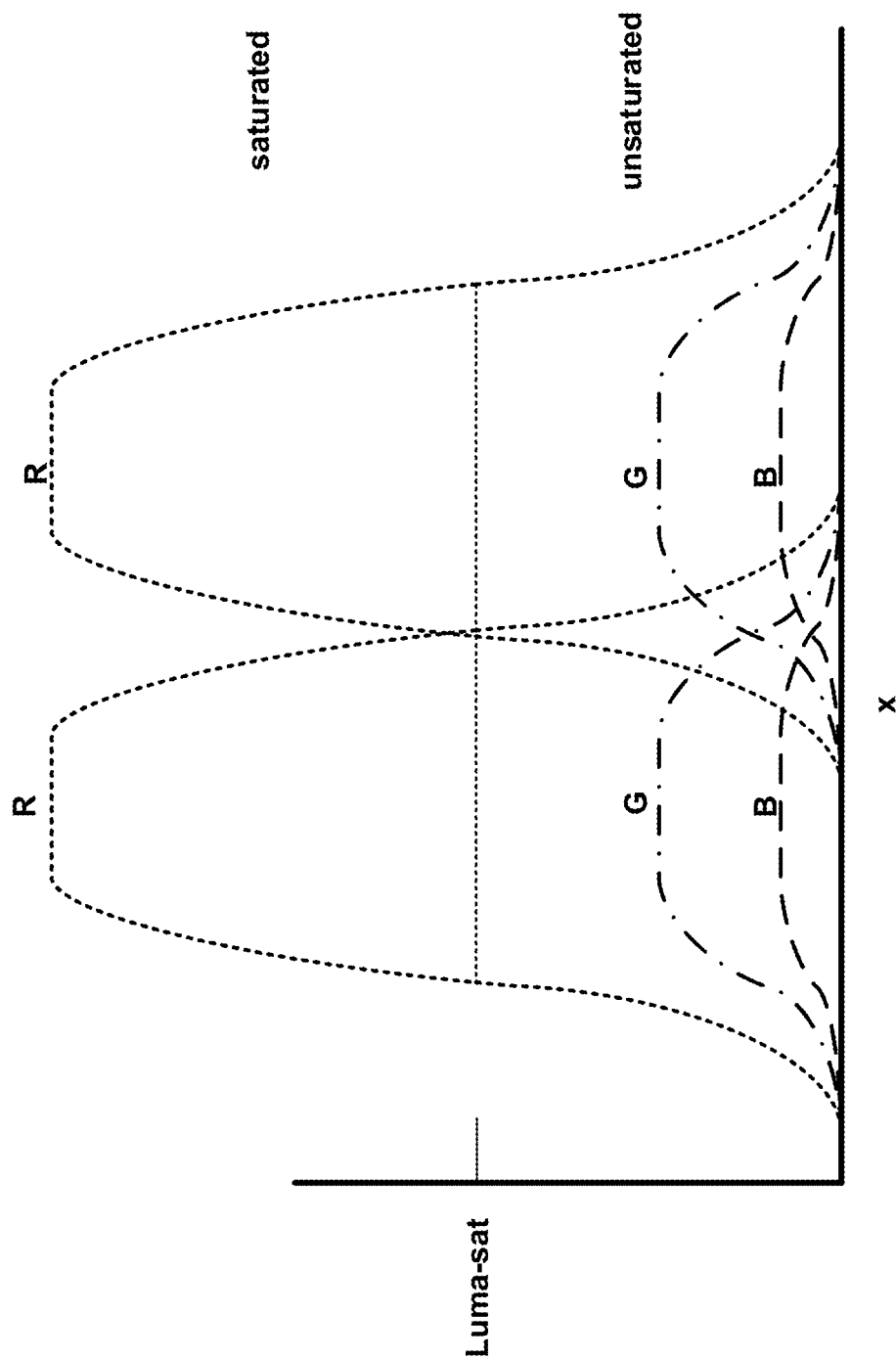
FIG. 14(A) and FIG. 14(B) are plots showing a sensor luma signal for R, G, and B pixels as a function of position x on the sensor for the cases FIG. 14(A) when an object is close to the endoscope and the irradiance on the sensor is high and FIG. 14(B) when an object is farther and the irradiance on the sensor is lower—according to aspects of the present disclosure.
Figure 14B:
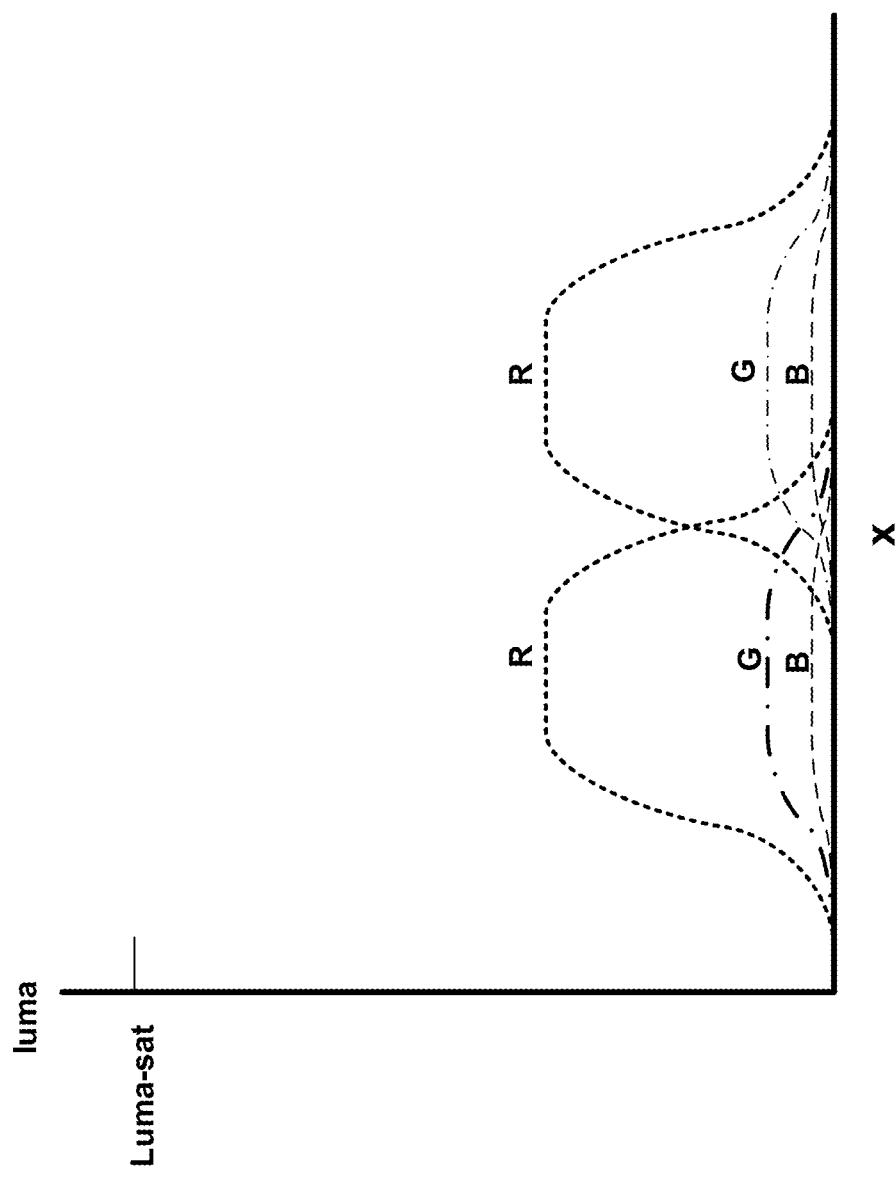

FIG. 14(A) and FIG. 14(B) shows the sensor luma signal for R, G, and B pixels as a function of position x on the sensor for the case FIG. 14(A) when an object is close to the endoscope and the irradiance on the sensor is high and the case FIG. 14(B) when an object is farther and the irradiance on the sensor is lower. The beams of light irradiating the mucosa object are assumed to be uniform over a certain area which appears in the image on the sensor as the regions of x over which the signal is plateaued. Due to tissue bulk scattering, the irradiance on the sensor does not fall off abruptly at the edge of these plateaus but extends more broadly over tails. The tails for two adjacent spots are shown to overlap. Diffuse background illumination from the SL source or another source also may contribute to the signal and push it towards saturation.

We note that the image sensor has a limited dynamic range and there is a maximum luma, luma-sat, corresponding to the maximum irradiance that can be recorded, for a particular sensor gain. Luma-sat is determined by the sensor analog to digital converter (ADC). For the case of a 10-bit ADC, the maximum luma is 1023 digital counts. With continued reference to FIG. 14(A) and FIG. 14(B), we note that in FIG. 14(A) the R pixel luma exceeds luma-sat and is saturated. Because the crossover point between the two spots is saturated, the image of the two spots has merged into a single spot so that the location of the two spots cannot be accurately determined from the R pixel signal. However, the G and B lumas are not saturated so that the spot locations can be determined from either or both of these signals.

For the situation illustrated in FIG. 14(B) the signals are weaker and none of the pixels is saturated. The R pixels have the best signal-to-noise ratio (SNR). Thus, the R signal is preferentially used to determine the spot locations. Additionally, the image may have a white-light signal (not shown) and the R channel is easier to distinguish from the white light image than the G or B as illustrated in FIG. 14(B). For the situation illustrated in FIG. 14(A) the saturated R signal can help to identify the presence of the SL spots in the presence of a WL background, but the spot centroids are more accurately determined from the G and B channels.

A sensor with pixels responsive to different color spectra, as opposed to a monochrome gray-scale sensor, increases the effective dynamic range of the SL detection if the response to the SL light is different but non-zero for at least two of the color channels. The channels can be combined into a single channel of increased dynamic range or analyzed separately. The example given is an RGB sensor, but other color channels could be used such yellow, clear (white), magenta, cyan, violet, or IR.

Figure 15:
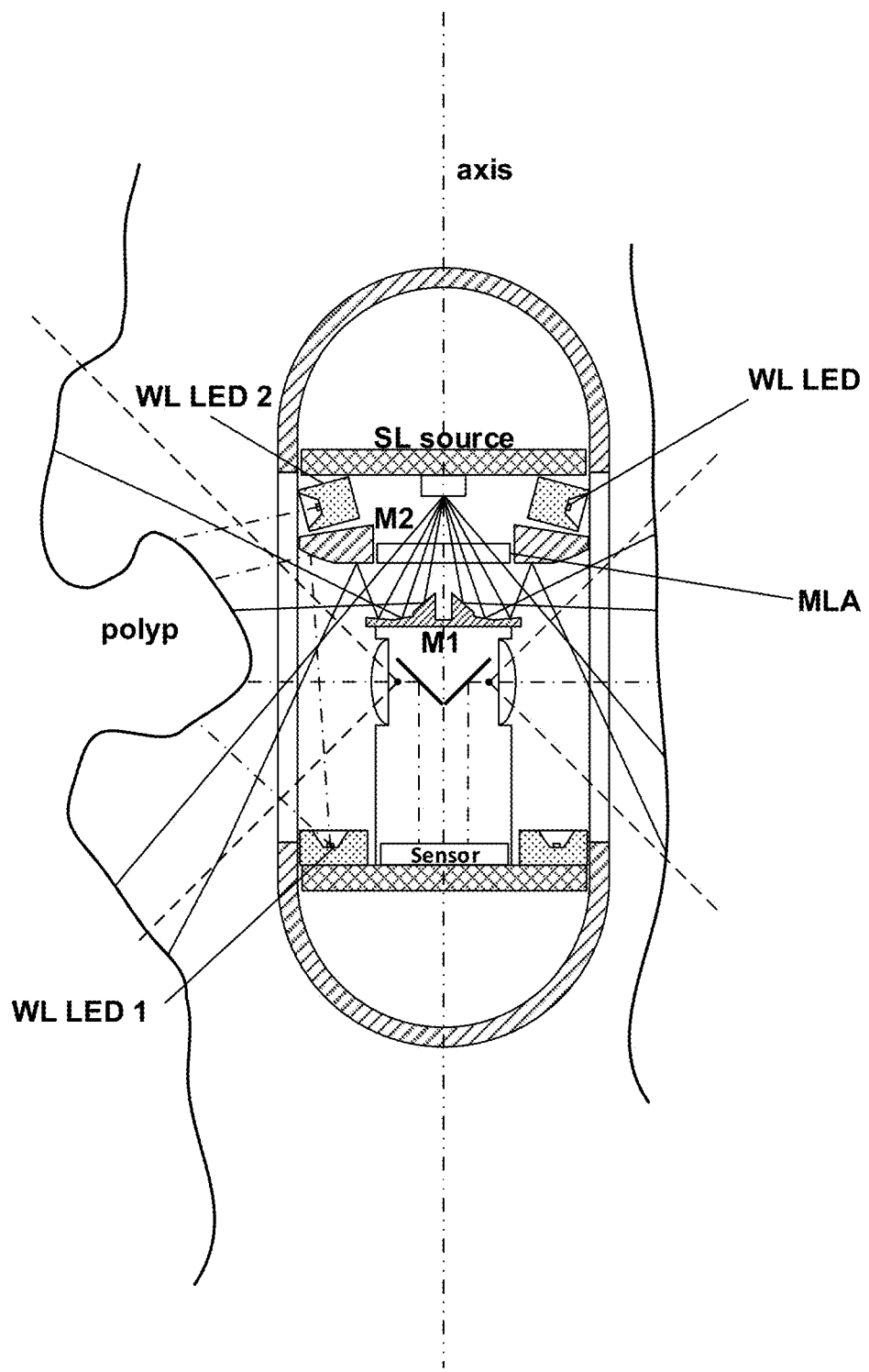
FIG. 15 is a schematic diagram of an illustrative capsule endoscope structure employing structured light plot inside a body lumen and a polyp according to aspects of the present disclosure.

FIG. 15 shows an illustrative capsule endoscope according to the present disclosure in a body lumen. The capsule has a tubular shaped middle section with two hemispherical endcaps. At least a portion of the tubular wall is transparent. The endoscope includes a panoramic imaging system that images through the tubular wall with four cameras. Four lens objectives face the tubular wall spaced approximately 90°. We note that while this example includes four cameras and four objectives, those skilled in the art will appreciate that a greater or lesser number of such elements may be employed so long as the desired FOV is achieved. Moreover, the same or similar apparatus, or a portion thereof, shown in FIG. 15 could be attached to an endoscope insertion tube at one end, as is shown for the apparatus in FIG. 9(A), yielding an insertion-type endoscope with panoramic imaging including depth measurement.

In this illustrative system the FOV of the imaging system is 360° about the capsule and from approximately 45° to 135° relative to the longitudinal axis. Mirrors within the lens module fold the optical axes of the lenses. In a particular illustrative embodiment, images are formed on a common image sensor, which may have pixels in four separate regions. The capsule includes white light LEDs or other sources for illuminating the lumen wall.

As illustratively shown in FIG. 15, two rays from WL LED 1 and one ray from WL LED 2 are shown illuminating the lumen wall. One ray from WL LED 1 reflects off mirror M2 before passing out of the tubular wall. A SL source, such as a point source LED, emits light in a broad distribution. The light is spatially filtered and collimated into beams by the MLA.

Illustratively, the MLA includes microlenses arrayed in substantially concentric rings such as that illustratively shown in FIG. 11. The mirror structure M1 comprises a plurality of annular reflective surface of various slopes. Advantageously, the surfaces could be conical or could have shapes curved in two dimensions. M2 is—in this illustrative embodiment—another annular mirror.

Shown further in FIG. 15 are chief rays of some of the beams that reflect off three annular surfaces of M1. Some of the beams reflect off M1 and then reflect again off M2. Reflective surfaces of M2 are used to reflect both SL beams and white light illumination from WL LED1 and direct both through the capsule housing to illuminate the lumen wall. M1 and M2 could be injection molded plastic parts with aluminum coatings. Note further that also shown in FIG. 15 are chief rays of beams which do not hit any mirror and pass directly from the MLA through the capsule housing.

As may be further observed in FIG. 15, a polyp is shown and illuminated, along with the lumen wall around it, by both white light, so that it may be visualized, identified, and demarcated in an image captured by the camera, and by SL, so that a depth map of the image may be generated, and the size of the polyp can be estimated. Beams at four different angles relative to the longitudinal axis of the capsule cover the FOV of the camera on the capsule housing's outer surface. Both SL beam angles greater than and less than 180 degrees are produced so that the panoramic field of view is covered. The beams travel both above and below a plane transverse to the capsule that includes the optical axes of the cameras. As noted previously, the number of cameras could be more or fewer than four—depending upon their particular FOV and any application requirements. Mirror M1 is shown with 3 conical annular surfaces but that number too, could be more or fewer.

Figure 16:
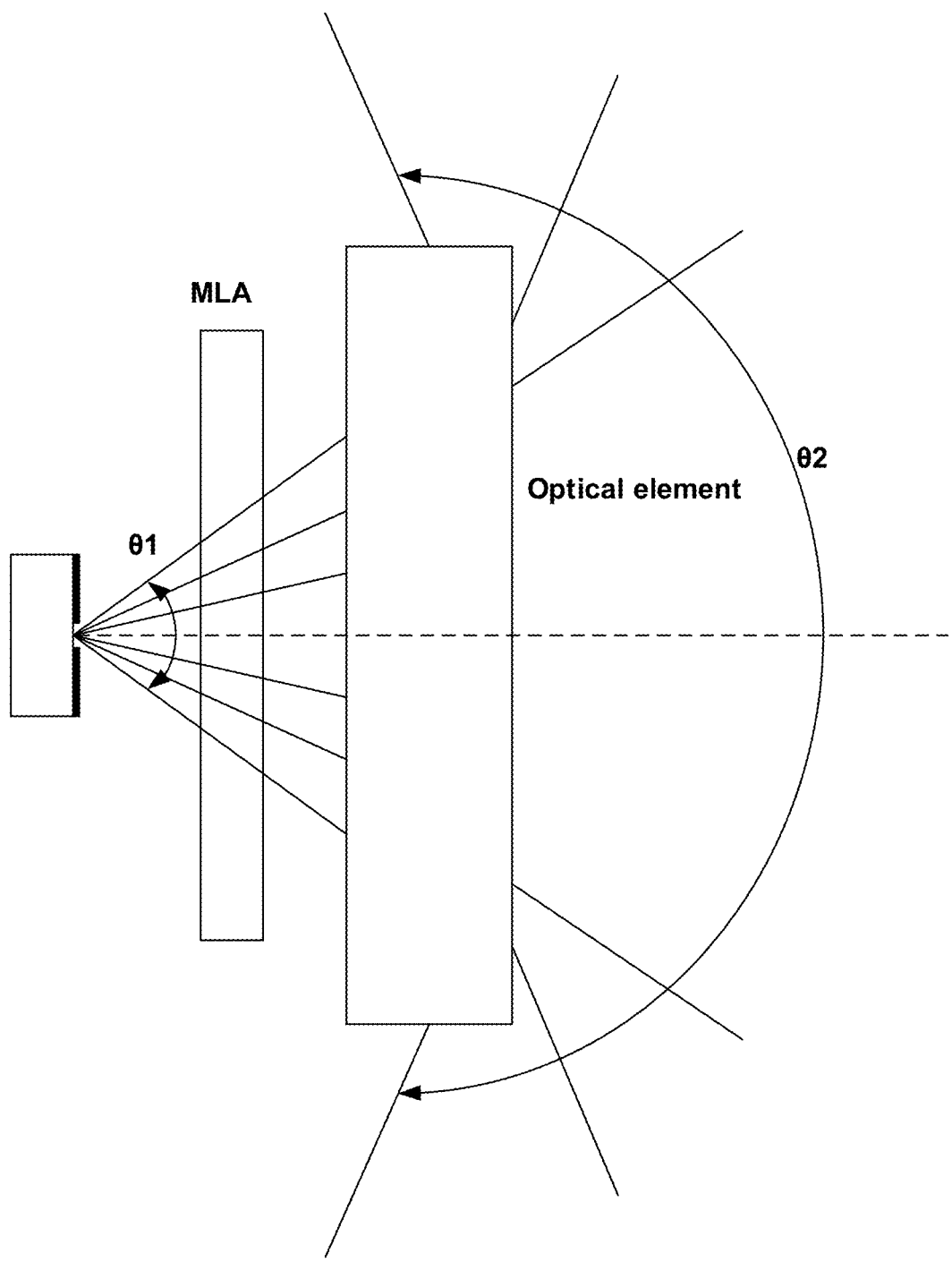
FIG. 16 is a schematic diagram of an illustrative endoscope configuration having an optical element following the MLA in an optical path according to aspects of the present disclosure.

As noted throughout this disclosure, endoscope configurations in which additional optical elements follow an MLA in an optical path may afford distinct advantages to those endoscopes. FIG. 16 is a schematic diagram showing an illustrative configuration wherein such optical element follows the MLA. One particular advantage of such configurations includes the ability to increase the range of angles over which structured light is projected from $\theta 1$ to $\theta 2$, which may exceed 180 degrees, as illustratively shown. The light source intensity may drop off significantly beyond $\theta 1$ and the throughput of the MLA decreases with increasing angle due to the foreshortening of the clear apertures and increased Fresnel loss. Moreover, the MLA cost may be larger than the optical element, so the arrangement of FIG. 16 minimizes the size of the MLA for a given lens focal length and desired FOV $\theta 2$. For endoscopes with panoramic imaging, an optical element yielding $\theta 2>180$ degrees enables one structured light projector to cover the entire camera panoramic FOV.

Figure 17:
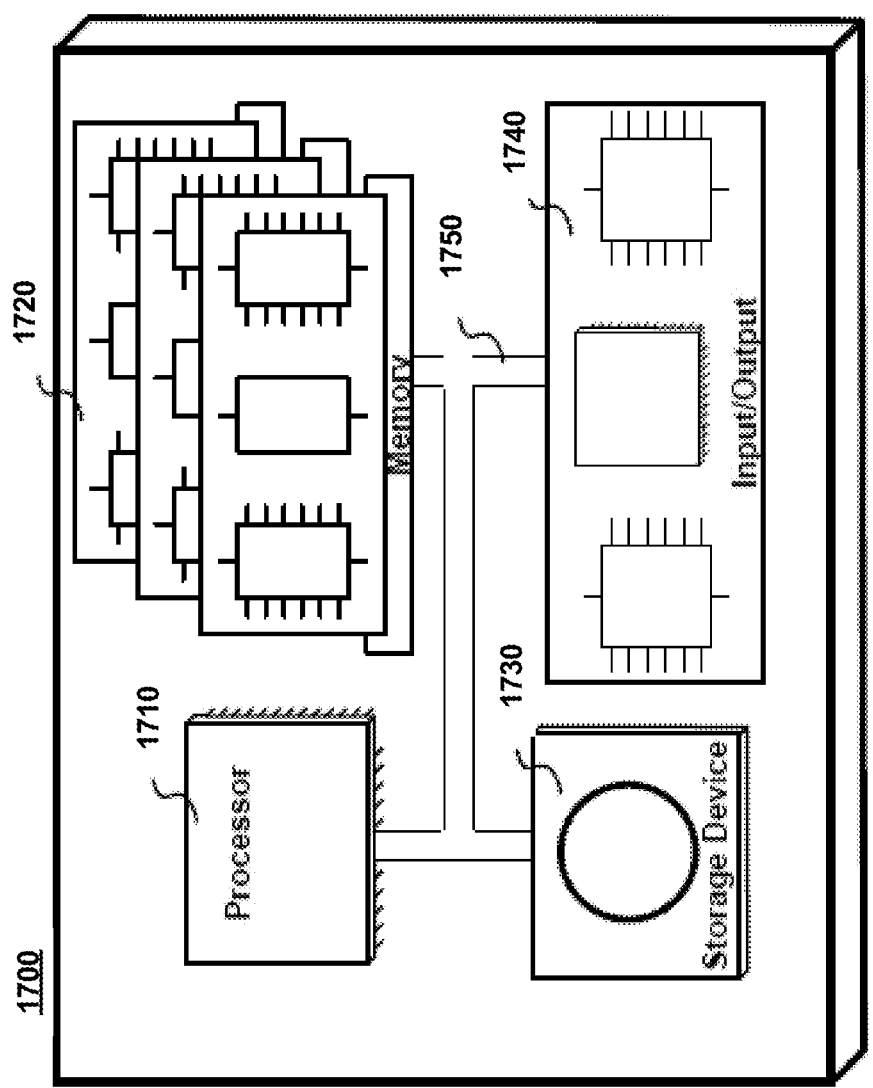
FIG. 17 is a schematic diagram of an illustrative computer system that may execute methods according to aspects of the present disclosure.

FIG. 17 shows an illustrative computer system 1700 suitable for implementing methods and systems according to an aspect of the present disclosure. The computer system may comprise, for example a computer running any of a number of operating systems or embedded control or application specific control programs. The above-described methods of the present disclosure may be implemented on the computer system 1700 as stored program control instructions. As will be readily appreciated by those skilled in the art, the specific computer system and components included therein may vary depending upon what specific aspect of the present disclosure is implemented thereon/therein.

Computer system 1700 includes processor 1710, memory 1720, storage device 1730, and input/output structure 1740. One or more input/output devices may include a display 1745. One or more busses 1750 typically interconnect the components, 1710, 1720, 1730, and 1740. Processor 1710 may be a single or multi core.

Processor 1710 executes instructions in which embodiments of the present disclosure may comprise steps described in one or more of the Figures. Such instructions may be stored in memory 1720 or storage device 1730. Data and/or information may be received and output using one or more input/output devices.

Memory 1720 may store data and may be a computer-readable medium, such as volatile or non-volatile memory. Storage device 1730 may provide storage for system 1700 including for example, the previously described methods. In various aspects, storage device 1730 may be a flash memory device, a disk drive, an optical disk device, or a tape device employing magnetic, optical, or other recording technologies.

Input/output structures 1740 may provide input/output operations for system 1700. Input/output devices utilizing these structures may include, for example, keyboards, displays 1745, pointing devices, and microphones—among others. As shown and may be readily appreciated by those skilled in the art, computer system 1700 for use with the present disclosure may be implemented in a desktop computer package 1760, a laptop computer 1770, a hand-held computer, for example a tablet computer, personal digital assistant or Smartphone 1780, or one or more server computers which may advantageously comprise a "cloud" computer 1790.

At this point, while we have presented this disclosure using some specific examples, those skilled in the art will recognize that our teachings are not so limited. More specifically, our methods can be further extended in that the structural events can embed more temporal information and consider more sophisticated structures including considering more finegrained temporal information, e.g., the transition time distribution, to enrich mined structural events. Also, we have focussed on transition relations among log patterns. There are other useful relations among logs, such as running in parallel that may be employed. Those relations can be further modeled in the workflow graph using undirected edges. We also believe that the methods according to the present disclosure can achieve more utility in an interactive setting, where system admins can interactively explore the system behaviors with different focusses (parameter settings) on coverage, quality or connectivity.

Accordingly, this disclosure should be only limited by the scope of the claims attached hereto.

The invention claimed is:

1. A method for imaging a body lumen comprising:
   introducing an imaging apparatus into the body lumen;
   emitting, during a common integration period of the imaging apparatus, from the imaging apparatus, structured light and non-structured light into the body lumen;
   detecting, by the imaging apparatus, both structured light and non-structured light reflected from anatomical features in the body lumen;
   generating, by the imaging apparatus, images from the detected light.

2. The method of claim 1 wherein each generated image is detected in an integration period, and the structured and non-structured light from which the image is generated is detected during that integration period.

3. The method of claim 2 wherein each integration period generates a single image frame of a video.

4. The method of claim 1 wherein the non-structured light is white light.

5. The method of claim 4 wherein the structured light exhibits an optical spectrum that is outside the white light spectrum.

6. The method of claim 1 wherein the structured light exhibits an optical spectrum that is different from the non-structured light.

7. The method of claim 1 wherein the imaging apparatus includes pixels that are transmissive to the structured light and less-transmissive of the non-structured light.

8. The method of claim 7 wherein the transmissivity of the imaging apparatus pixels are light wavelength-dependent.

9. The method of claim 1 wherein the imaging apparatus includes pixels that are configured to block transmission of the non-structured light.

10. The method of claim 1 further comprising:
    before introducing the capsule endoscope into the body lumen:
      projecting a structured light pattern emanating from the capsule onto a scene;
      generating calibration data from that projected pattern; and
      storing the calibration data into a memory.

11. The method of claim 10 further comprising capturing at least one image to generate said calibration data.

12. The method of claim 11 further comprising storing the generated calibration date in a memory, wherein the memory is located within the capsule endoscope.

13. The method of claim 1 further comprising removing detected structured light from the generated images.

14. The method of claim 13 wherein the removing is performed prior to a displaying of the images.

15. The method of claim 13 wherein images from which reflected structured light has been removed are displayed as gray-scale image(s).

16. The method of claim 1 further comprising:
    identifying an object of interest in a non-structured light frame and structured light frame; and
    selecting a proximal structured light frame such that a size of the object may be estimated/determined.

* * * * *